United States Patent
Lenee et al.

(10) Patent No.: US 6,646,117 B1
(45) Date of Patent: *Nov. 11, 2003

(54) POLYRIBOZYME CAPABLE OF CONFERRING ON PLANTS RESISTANCE TO VIRUSES AND RESISTANT PLANTS PRODUCING THIS POLYRIBOZYME

(75) Inventors: Philippe Lenee, Les Vigneaux (FR); Pascual Perez, Beaumont (FR); Veronique Gruber, Chamalieres (FR); Gaelle Baudot, Clermont-Ferrand (FR); Catherine Ollivo, Riom (FR)

(73) Assignee: Gene Shears. Pty. Limited, Canberra (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/705,014

(22) Filed: Nov. 2, 2000

Related U.S. Application Data

(63) Continuation of application No. 08/507,426, filed as application No. PCT/FR94/00216 on Feb. 25, 1994, now Pat. No. 6,265,634.

(30) Foreign Application Priority Data

Feb. 26, 1993 (FR) ............................................ 93 02269

(51) Int. Cl.[7] ............................ C12Q 1/68; C07H 2/04; A01H 1/00; A01H 5/00; C12N 15/85
(52) U.S. Cl. ......................... 536/24.5; 435/6; 435/91.3; 800/279; 800/285; 800/301
(58) Field of Search ........................ 435/6, 91.3, 91.31, 435/320.1, 419, 468, 469; 536/23.1, 24.3, 24.5; 800/279, 285, 301

(56) References Cited

U.S. PATENT DOCUMENTS

| | | | |
|---|---|---|---|
| 5,500,357 A | | 3/1996 | Taira |
| 6,265,634 B1 | * | 7/2001 | Lenee et al. ................. 800/279 |

OTHER PUBLICATIONS

Report and recommendations of the panel to assess the NIH investment in research on gene therapy, Orkin and Motulsky, co–chairs. National Institutes of Health (12/95).*
Gewirtz et al. Facilitating oligonucleotide delivery: Helping antisense deliver on its promise. Proc. Natl. Acad. Sci. USA 93: 3161–3163 (4/96).*
Stull et al. Antigene, ribozyme and aptamer nucleic acid drugs: Progress and prospects. Pharm. Res. 12: 465–483 (4/95).*
Burke, Clearing the way for ribozymes, Nat. Biotechnol. 15:414–415, (May 1997) (Exhibit 2).
Chen et al., Multitarget–ribozyme directed to cleave at up to nine highly conserved HIV–1 env RNA regions inhibits HIV–1 replication—potential effectiveness against most presently sequenced HIV–1 isolates, Nucleic Acids Res. 20(17):4581–4589 (Sep. 1992) (Exhibit 3).
Cuozzo et al., Viral protection in transgenic tobacco plants expressing the cucumber mosaic virus coat protein or its antisense RNA, Bio/Technology 6:549–557, (May 1988) (Exhibit 4).
Day et al., Expression of an antisense viral gene in transgenic tobacco confers resistant to the DNA virus tomato golden mosaic virus, Proc. Natl. Acad. Sci. USA vol. 88, pp. 6721–6725, (1991) (Exhibit 5).
Edington et al., Utilization of ribozymes in plants in "Gene regulation: Biology of Antisense RNA and DNA," Erickson et al., eds. Raven Press, Ltd, New York, pp. 209–221 (1992) (Exhibit 6).
Golemboski et al., Plants transformed with a tobacco mosaic virus nonstructural gene sequence are resistant to the virus, Proc. Natl. Acad. Sci. USA, vol. 87, pp. 6311–6315 (1990) (Exhibit 7).
Hemenway et al., Analysis of the mechanism of protection in transgenic plants expressing the potato virus X coat protein or its antisense RNA, The EMBO Journal vol. 7, No. 5, pp. 1273–1280, (1988) (Exhibit 8).
Lamb et al., Ribozymes that cleave potato leafroll virus RNA within the coat protein and polymerase genes. J. Gen. Virol. 71:2257–2264 (1990) (Exhibit 9).
Nelson et al., Tobacco mosaic virus infection of transgenic *Nicotiana tabacum* plants is inhibited by antisense constructs directed at the 5' region of vial RNA, Gene, 127, pp. 227–232 (1993) (Exhibit 10).
Powell et al., Protection against tobacco mosaic virus in transgenic plants that express tobacco mosaic virus antisense RNA, Proc. Natl. Acad. Sci. vol. 86, pp. 6949–6952, (1989) (Exhibit 11).
Rezaian et al., Anti–sense RNAs of cucumber mosaic virus in transgenic plants assessed for control of the virus, Plants Molecular Biology 11:463–471 (1988) (Exhibit 12).
Van de Elzen et al., Engineering virus resistance in agricultural crops, Plant Molecular Biology 13:337–346, (1989) (Exhibit 13).
Wolter et al., Biochmeische und molekularbiologische Ansatze zur Veranderung der Fettsaurezusammensetzung des Rapsols, Fat Sci. Technol. 93, Jahrgang Nr. 8 (1991) (Exhibit 14). English Abstract Only.

* cited by examiner

Primary Examiner—Sean McGarry
Assistant Examiner—Karen A Lacourciere
(74) Attorney, Agent, or Firm—John P. White; Cooper & Dunham LLP

(57) ABSTRACT

The invention relates to a nucleic acid sequence, called "polyribozyme", which has an endoribonuclease activity and is capable of inactivating the gene for the capsid protein of a virus, characterized in that it comprises:

Figure 1A:
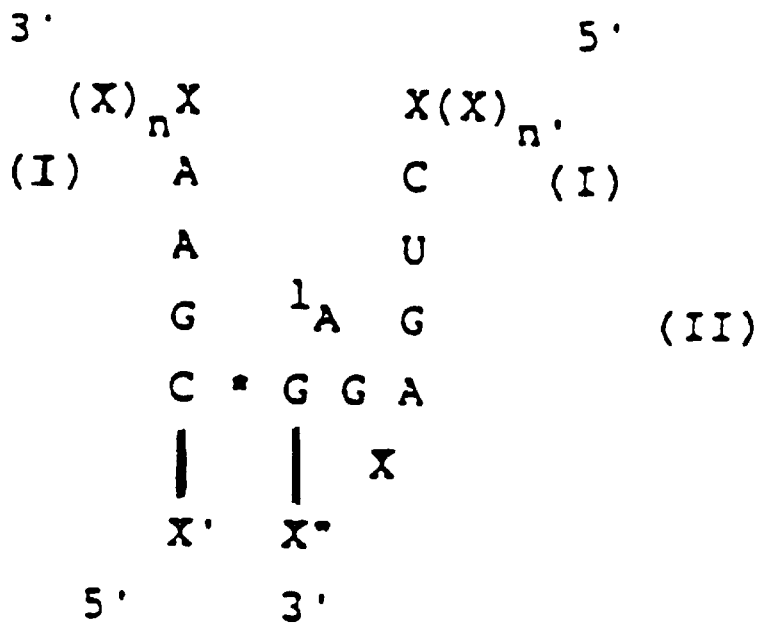

i) a sequence complementary to at least a part of the gene or its transcript or to its replication intermediates and, includes at distinct sites in this complementary sequence:

ii) a plurality of ribozyme catalytic regions;

iii) and, optionally, one or more sequences non-complementary to the transcript of the said gene, the said non-complementary sequence(s) being inserted between two consecutive bases of the complementary sequence.

21 Claims, 11 Drawing Sheets

FIGURE 2

```
AGAGAGTGTGTGTGCTGTGTTTTCTCTTTTGTGTCGTAGAATTGAGTCGAG                51
     Oligo n°13
5'─────────────────────────────→3'                              84
TC ATG GAC AAA TCT GAA TCA ACC AGT GCT GGT CGT AAC               89
   Met Asp Lys Ser Glu Ser Thr Ser Ala Gly Arg Asn               12
                        108
CGT CGA CGT CGT CCG CGT CGT GGT TCC CGC TCC GCC CCC              128
Arg Arg Arg Arg Pro Arg Arg Gly Ser Arg Ser Ala Pro               25
TCC TCC GCG GAT GCT AAC TTT AGA GTC TTG TCG CAG CAG              167
Ser Ser Ala Asp Ala Asn Phe Arg Val Leu Ser Gln Gln               38
                                            204
CTT TCG CGA CTT AAT AAG ACG TTA GCA GCT GGT CGT CCA              206
Leu Ser Arg Leu Asn Lys Thr Leu Ala Ala Gly Arg Pro               51
ACT ATT AAC CAC CCA ACC TTT GTA GGG AGT GAA CGC TGT              245
Thr Ile Asn His Pro Thr Phe Val Gly Ser Glu Arg Cys               64
AGA CCT GGG TAC ACG TTC ACA TCT ATT ACC CTA AAG CCA              284
Arg Pro Gly Tyr Thr Phe Thr Ser Ile Thr Leu Lys Pro               77
CCA AAA ATA GAC CGT GGG TCT TAT TAC GGT AAA AGG TTG              323
Pro Lys Ile Asp Arg Gly Ser Tyr Tyr Gly Lys Arg Leu               90
                                        357  Hind III
TTA CTA CCT GAT TCA GTC ACG GAA TAT GAT AAG AAG CTT              362
Leu Leu Pro Asp Ser Val Thr Glu Tyr Asp Lys Lys Leu              103
GTT TCG CGC ATT CAA ATT CGA GTT AAT CCT TTG CCG AAA              401
Val Ser Arg Ile Gln Ile Arg Val Asn Pro Leu Pro Lys              116
TTT GAT TCT ACC GTG TGG GTG ACA GTC CGT AAA GTT CCT              440
Phe Asp Ser Thr Val Trp Val Thr Val Arg Lys Val Pro              129
GCC TCC TCG GAC TTA TCC GTT GCC GCC ATC TCT GCT ATG              479
Ala Ser Ser Asp Leu Ser Val Ala Ala Ile Ser Ala Met              142
TTC GCG GAC GGA GCC TCA CCG GTA CTG GTT TAT CAG TAT              518
Phe Ala Asp Gly Ala Ser Pro Val Leu Val Tyr Gln Tyr              155
GCC GCA TCT GGA GTC CAA GCC AAC AAC AAA CTG TTG TAT              557
Ala Ala Ser Gly Val Gln Ala Asn Asn Lys Leu Leu Tyr              168
GAT CTT TCG GCG ATG CGC GCT GAT ATA GGT GAC ATG AGA              596
Asp Leu Ser Ala Met Arg Ala Asp Ile Gly Asp Met Arg              181
            608
AAG TAC GCC GTC CTC GTG TAT TCA AAA GAC GAT GCG CTA              635
Lys Tyr Ala Val Leu Val Tyr Ser Lys Asp Asp Ala Leu              194
GAG ACG GAC GAG CTA GTA CTT CAT GTT GAC ATC GAG CAC              674
Glu Thr Asp Glu Leu Val Leu His Val Asp Ile Glu His              207
         Oligo n°14
3'←─────────────────────5'
CAA CGC ATT CCC ACG TCT GGA GTG CTC CCA GTC TGATTCGT             715
Gln Arg Ile Pro Thr Ser Gly Val Leu Pro Val                      218

GTTCCCAGAATCCTCCCTCCGATCTCTGTGGCGGGAGCTGAGTTGGCAGTTC             767
TGCTATAAACTGTCTGAAGTCACTAAACGTTTTTACGGTGAACGGGTTGTCC             819
ATCCAGCTTACGGCTAAAATGGTCAGTCGTGGAGAAATCCACGCCAGTAGAT             871
TTACAAATCTCTGAGGCGCCTTTGAAACCATCTCCTAGGTTTCTTCGGAAGG             923
ACTTCGGTCCGTGTACCTCTAGCACAACGTGCTAGTTTCAGGGTACGGGTGC             975
CCCCCCACTTTCGTGGGGGCCTCCAAAAGGAG                                 1007
```

FIGURE 3
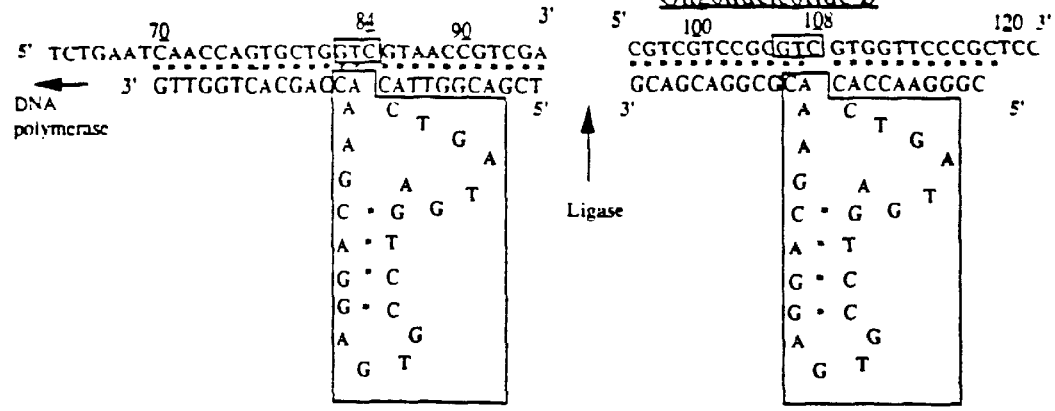
Oligonucléotide A / Oligonucléotide B
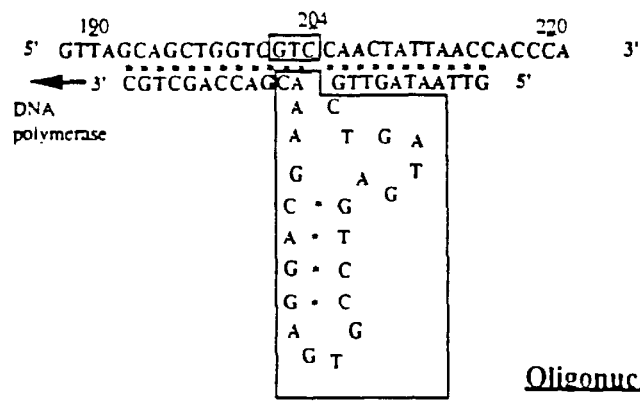
Oligonucléotide C
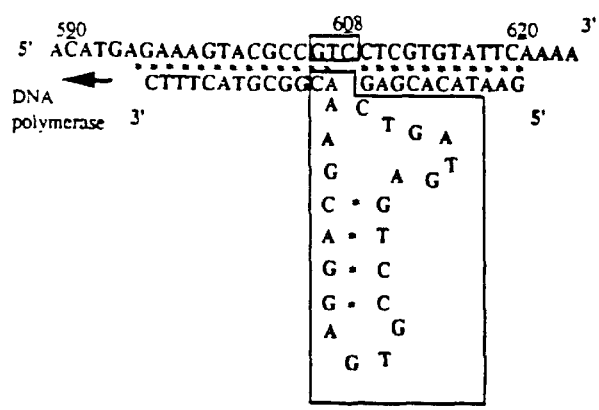
Oligonucléotide E

FIGURE 4
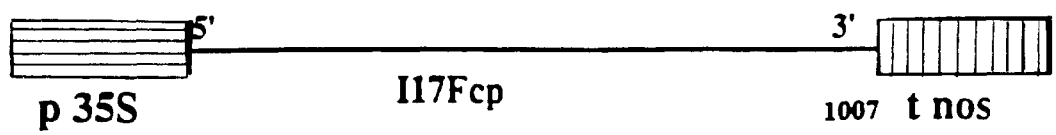
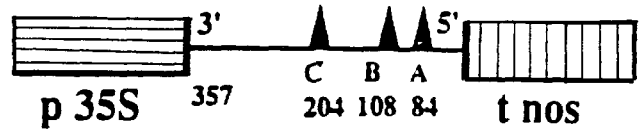

FIGURE 6
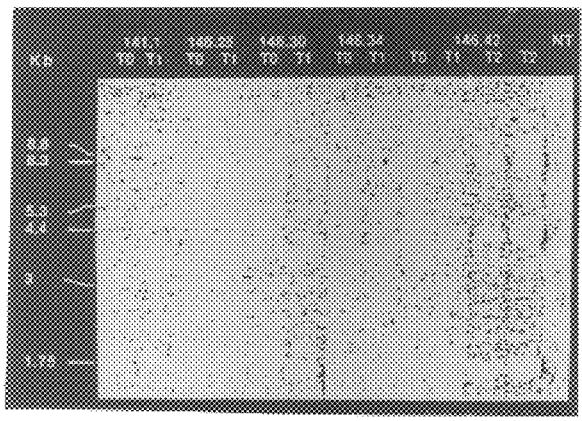
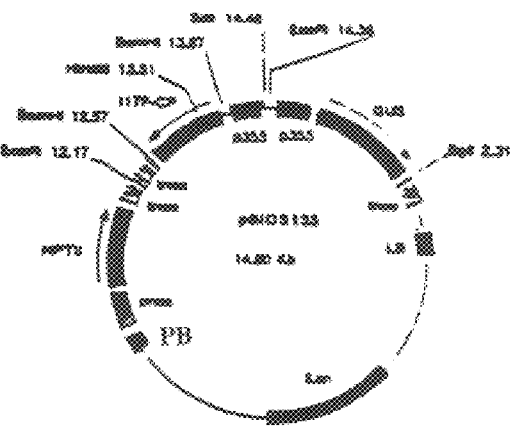
probe 117F - cp
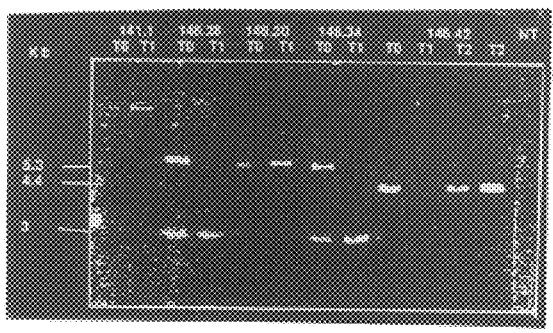
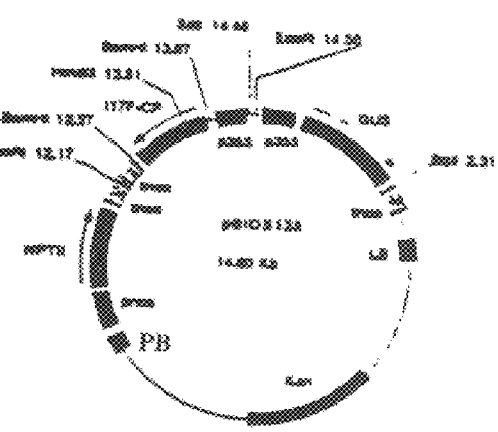
probe npt II
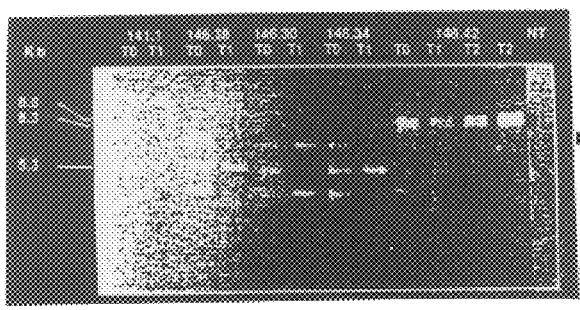
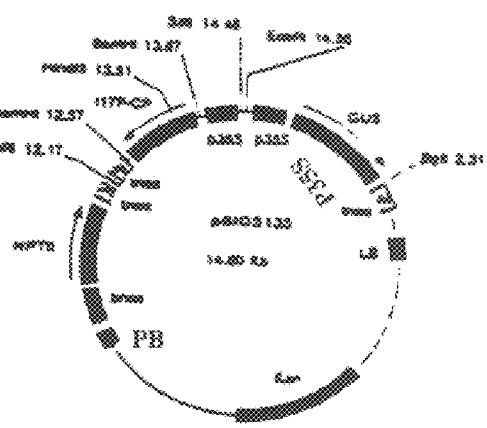
probe gus

FIGURE 7
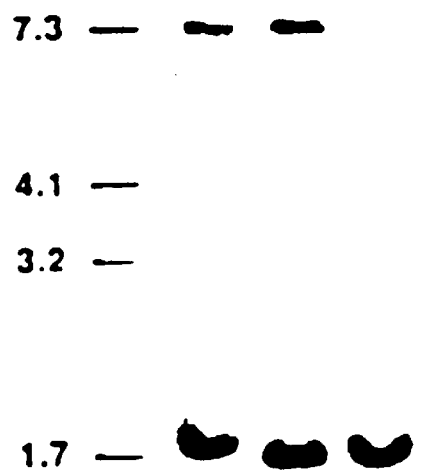
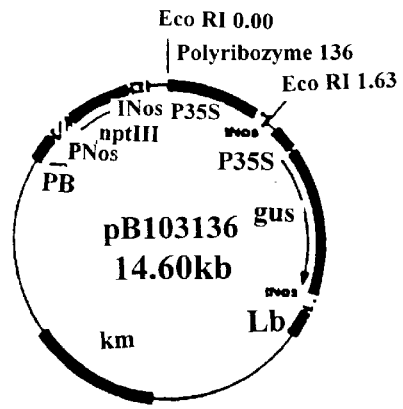
pro polyribozyme 136
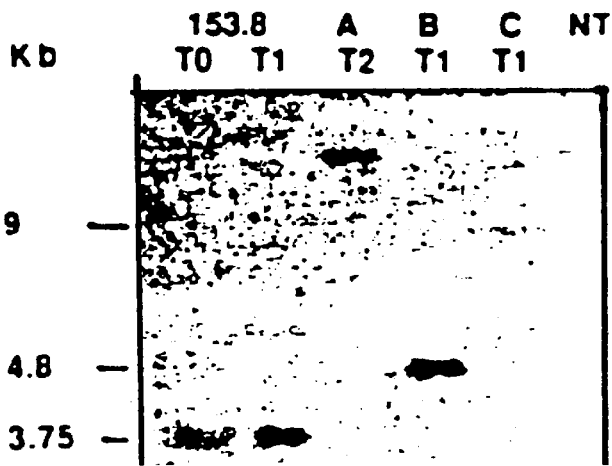
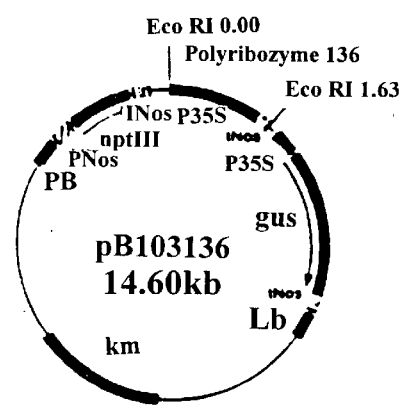
pro npt II
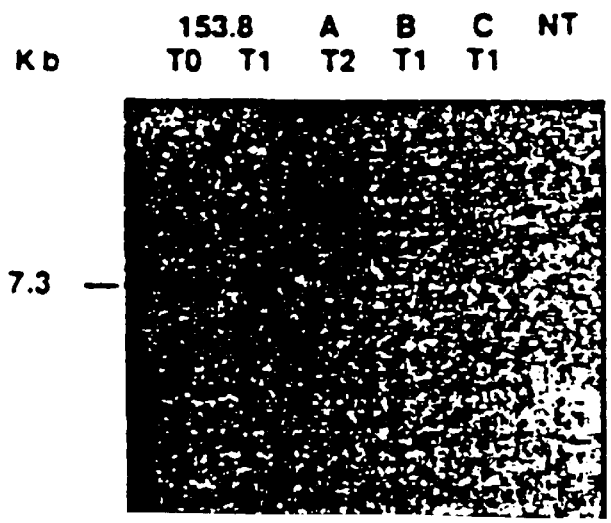
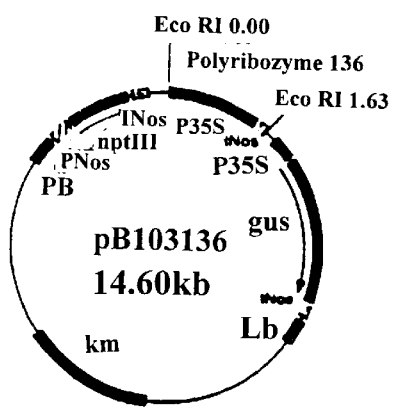
probe gus

FIGURE 10
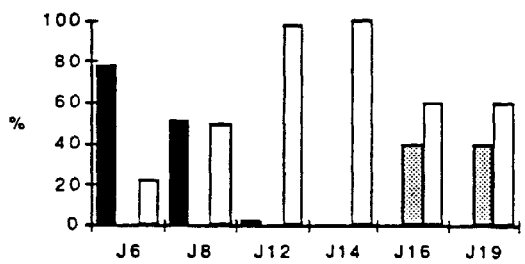
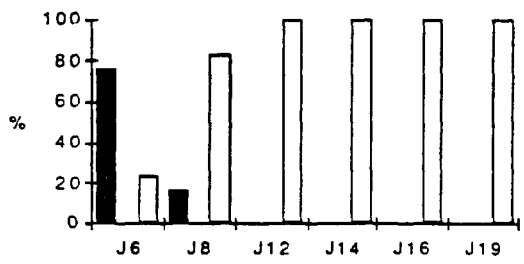
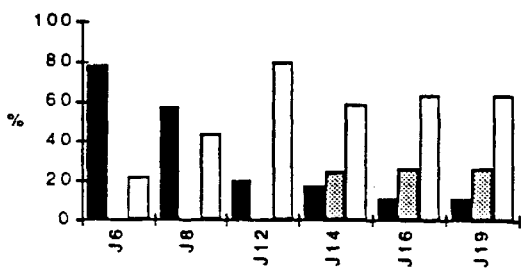
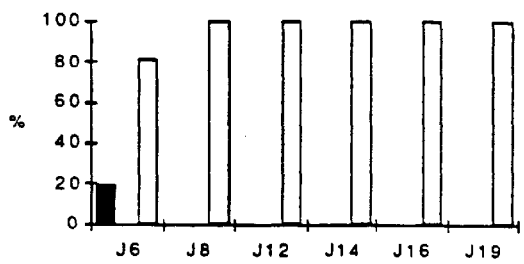
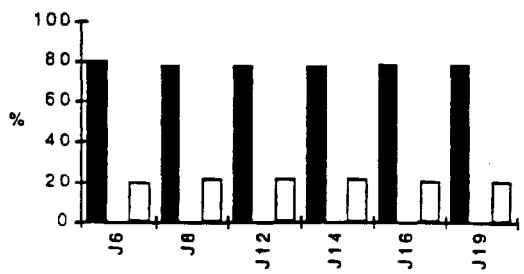
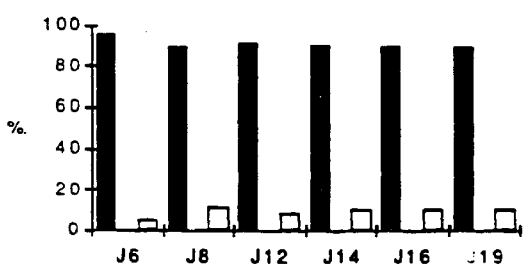

SEQUENCE LISTING

<160> NUMBER OF SEQ ID NOS: 14

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence:Synthetic
      ribozymes and portions thereof

<400> SEQUENCE: 1
tcgacggtta cctgatgagt ccgtgaggac gaaaccagca ctggttg          47

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence:Synthetic
      ribozymes and portions thereof

<400> SEQUENCE: 2
cgggaaccac ctgatgagtc cgtgaggacg aaacgcggac gacg             44

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence:Synthetic
      ribozymes and portions thereof

<400> SEQUENCE: 3
gttaatagtt gctgatgagt ccgtgaggac gaaacgacca gctgc            45

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence:Synthetic
      ribozymes and portions thereof

<400> SEQUENCE: 4
gaatacacga gctgatgagt ccgtgaggac gaaacggcgt actttc           46

<210> SEQ ID NO 5
<211> LENGTH: 1007
<212> TYPE: DNA
<213> ORGANISM: Artificial Sequence
<220> FEATURE:
<223> OTHER INFORMATION: Description of Artificial Sequence:Synthetic
      ribozymes and portions thereof

<400> SEQUENCE: 5
agagagtgtg tgtgctgtgt tttctctttt gtgtcgtaga attgagtcga gtcatggaca      60
aatctgaatc aaccagtgct ggtcgtaacc gtcgacgtcg tccgcgtcgt ggttcccgct     120 ccgcccctc ctccgcggat gctaacttta gagtcttgtc gcagcatctt tcgcgactta     180
ataagacgtt agcagctggt cgtccaacta ttaaccaccc aacctttgta gggagtgaac     240
gctgtagacc tgggtacacg ttcacatcta ttacccctaaa gccaccaaaa atagaccgtg     300
ggtcttatta cggtaaaagg ttgttactac ctgattcagt cacggaatat gataagaagc     360

```
ttgtttcgcg cattcaaatt cgagttaatc ctttgccgaa atttgattct accgtgtggg    420
tgacagtccg taaagttcct gcctcctcgg acttatccgt tgccgccatc tctgctatgt    480
tcgcggacgg agcctcaccg gtactggttt atcagtatgc cgcatctgga gtccaagcca    540
acaacaaact gttgtatgat ctttcggcga tgcgcgctga tataggtgac atgagaaagt    600
acgccgtcct cgtgtattca aaagacgatg cgctagagac ggacgagcta gtacttcatg    660
ttgacatcga gcaccaacgc attcccacgt ctggagtgct cccagtctga ttcgtgttcc    720
cagaatcctc cctccgatct ctgtggcggg agctgagttg gcagttctgc tataaactgt    780
ctgaagtcac taaacgtttt tacggtgaac gggttgtcca tccagcttac ggctaaaatg    840
gtcagtcgtg gagaaatcca cgccagtaga tttacaaatc tctgaggcgc ctttgaaacc    900
atctcctagg tttcttcgga aggacttcgg tccgtgtacc tctagcacaa cgtgctagtt    960
tcagggtacg ggtgcccccc cactttcgtg ggggcctcca aaaggag                1007
```

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:Synthetic
      ribozymes and portions thereof

<400> SEQUENCE: 6

```
tctgaatcaa ccagtgctgg tcgtaaccgt cga                                 33
```

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence:Synthetic
      ribozymes and portions thereof

<400> SEQUENCE: 7

```
gttggtcacg accaaagcag gagtgcctga gtagtccatt ggcagct                  47
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:Synthetic
      ribozymes and portions thereof

<400> SEQUENCE: 8

```
cgtcgtccgc gtcgtggttc ccgctcc                                        27
```

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence:Synthetic
      ribozymes and portions thereof

<400> SEQUENCE: 9

```
gcagcaggcg caaagcagga gtgcctgagt cgtccaccaa gggc                     44
```

<210> SEQ ID NO 10
<211> LENGTH: 33
<212> TYPE: DNA
<213> ORGANISM: Artificial Sequence -continued

```
<220> FEATURE:
<223> OTHER INFORMATION: Description of Artificial Sequence:Synthetic
      ribozymes and portions thereof

<400> SEQUENCE: 10
gttagcagct ggtcgtcaac tattaaccac cca                                33

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence:Synthetic
      ribozymes and portions thereof

<400> SEQUENCE: 11
cgtcgaccag caaagcagga gtgcctgagt agtcgttgat aattg                   45

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence:Synthetic
      ribozymes and portions thereof

<400> SEQUENCE: 12
acatgagaaa gtacgccgtc ctcgtgtatt caaaa                              35

<210> SEQ ID NO 13
<211> LENGTH: 46
<212> TYPE: DNA
<213> ORGANISM: Artificial Sequence
<220> FEATURE:
<223> OTHER INFORMATION: Description of Artificial Sequence:Synthetic
      ribozymes and portions thereof

<400> SEQUENCE: 13
ctttcatgcg gcaaagcagg agtgcctgag tagtcgagca cataag                  46

<210> SEQ ID NO 14
<211> LENGTH: 36
<212> TYPE: RNA
<213> ORGANISM: Artificial Sequence
<220> FEATURE:
<223> OTHER INFORMATION: n=g, a, c or t(u)
<223> OTHER INFORMATION: Description of Artificial Sequence:Synthetic
      ribozymes and portions thereof

<400> SEQUENCE: 14
nnnnnncuga ugaguccgug aggacgaaac nnnnnn                             36
```

POLYRIBOZYME CAPABLE OF CONFERRING ON PLANTS RESISTANCE TO VIRUSES AND RESISTANT PLANTS PRODUCING THIS POLYRIBOZYME

This application is a continuation of U.S. Ser. No. 08/507,426, now U.S. Pat. No. 6,265,634, filed Oct. 25, 1995, which is a §371 National Stage of PCT International Application No. PCT/FR94/00216, filed Feb. 25, 1994, which claims, priority of French Application No. 93 02269 filed Feb. 26, 1993.

The present invention relates to a nucleotide sequence, called "polyribozyme", capable of conferring on plants resistance to viruses, as well as a process for making the plants resistant. The invention also relates to the plants expressing the polyribozyme.

Several approaches have been developed to confer on cultivated plants resistance to viruses by integrating into the genome of the plants viral nucleic acid sequences: the gene for the capsid protein, the genes for non-structural proteins, anti-sense viral RNA sequences and RNAs of satellite viruses (see, for example, Cuozzo et al., 1988, Bio/Technology 6, 549–557; Rezaian et al., 1988, Plant. Mol. Biol., 11, 463–471; Harrison et al., 1987, Nature 328, 797–802).

These publications report the production of partial resistances or tolerances. Nonetheless, in most cases there are delayed symptoms or attenuated symptoms but not complete resistance.

Furthermore, some of these procedures, for example those employing the RNAs of satellite viruses, can give rise to new problems. For example, a satellite virus which reduces symptoms in one species may become lethal for another species. Moreover, mutations in the nucleotide sequences of the satellite virus introduced into the plants may increase the severity of the infection instead of diminishing it.

Similarly, the use of the capsid protein to confer resistance has disadvantages. For example, the capsid protein of a particular strain of the virus does not necessarily protect the plant against an infection by another strain of the virus. It is difficult to use the degree of homology of the amino acid sequence of the capsid protein between different viruses or between different strains to predict the degree of tolerance allowed by the expression of the protein. Furthermore, the expression of capsid proteins to protect against viral infection presents the risk of inducing heteroencapsidation between the capsid protein expressed in the plant and other viruses infecting the transgenic plant. Although it has never been demonstrated for transgenic plants, this heteroencapsidation has already been observed between two strains of BYDV and between ZYMV and PRSV.

The use of ribozymes has also been considered for conferring on plants resistance to viruses. Ribozymes are RNA molecules which act as enzymes by specifically catalysing the cleavage of the target RNA. The first experiments with ribozymes in plant cells were described in the patent application EP-A-321021. Since then, several authors have tried to optimise the structure of the ribozyme and the operating conditions in order to obtain efficient cleavage of the viral RNA.

For example, Lamb and Hay (J. Gen. Virol., 1990, 71:2257–2264) have demonstrated the in vitro cleavage by mono-ribozymes of the RNA of the Potato Leaf Roll virus (PLRV) in regions coding for the RNA polymerase and the capsid protein. However, the in vitro cleavage reaction only occurs at 40° C.; it has not been possible to observe any reaction at all at 0° C. Plants are usually cultivated between 10 and 30° C., depending on the species. Thus, for in vivo use, Lamb and Hay suggest that the length of the complementary arms be increased. But, if the arms are too long, the formation of a stable duplex between the target RNA and the ribozyme can be caused, preventing the dissociation of the ribozyme and making it incapable of catalysing another cleavage reaction. Furthermore, depending on the length and sequence of the complementary arms, the ribozyme itself may form secondary structures which diminish its cleavage activity.

Edington and Nelson ("Gene Regulation: Biology of Antisense RNA and DNA: Ed. ERICKSON and IZANT, Raven Press Ltd, New-York, 1992) have described the in vitro and in vivo use of mono- ribozymes to inactivate the polymerase gene of the Tobacco Mosaic virus (TMV). They observed that the ribozymes exhibited a very different behaviour depending on whether they were used in vitro or in vivo. The activity of a ribozyme in vitro can not thus be used to predict the activity of the same ribozyme in vivo. For example, in vitro cleavage appear to be of low efficiency and requires a ribozyme concentration 20 times higher than the concentration of the TMV genomic RNA. On the other hand, in an in vivo experiment using tobacco protoplasts infected by TMV, the ribozyme suppresses 90% of the multiplication of the viral RNA. It is interesting to note that the anti-sense RNA used as control only inhibits 20% of the viral multiplication. These workers also refer to the studies of Gerlach et al. who made use of a polyribozyme targeted against the gene for the polymerase of TMV. This polyribozyme did not function in vitro owing to the length of the duplex formed between the ribozyme and the target RNA. On the other hand, in vivo, this polyribozyme cleaved the substrate. Transgenic tobacco plants expressing either the monoribozyme or the polyribozyme have shown a delay of symptoms after infection by the TMV. Complete resistance, i.e. the definitive absence of symptoms, is not described. The authors conclude that the parameters such as the optimal length of the complementary arms, the choice of the target sequence and the choice of the promoter, enabling possible problems of "compartment-alisation" of the ribozymes to be overcome, must be determined by experiment.

EP-A-0421376 describes ribozymes directed against a non-coding RNA sequence of CMV. WO-A-9213090 describes the inactivation of the RNA of the capsid protein of the CMV by the introduction of a heterologous sequence within the sequence using a monoribozyme of the "Group I intron" type. None of these documents describes the production of complete resistance to the CMV.

The technical problem which the present invention proposes to resolve is to provide a reliable agent, devoid of disadvantages, for conferring on plants resistance to viruses.

The present inventors have resolved this problem by the conception and use of a polyribozyme directed against the capsid protein of a virus. This polyribozyme is capable of inactivating the gene coding for this protein, and of thus conferring complete resistance to viruses.

The efficiency of the polyribozyme of the invention is surprising in the light of the mediocre results obtained in the prior art with the anti-sense sequences of the gene for the capsid protein, since each of these procedures involves an inactivation of the corresponding RNA. In addition, several authors had advised against the use of trans acting polyribozymes because the ribozymes are unable to function independently of each other and because catalytic regions having identical sequences sometimes have a tendency to hybridize to each other, which leads to inactive structures (see, for example, Taira, HFSP. Workshop "RNA- Editing—Plant Mitochondria", Abstract Book, Berlin, Sep. 15–20, 1992). The results obtained according to the invention are unexpected in view of the target selected, on the one hand, i.e. the capsid protein and, on the other hand, the method used to inactivate the target, i.e. a polyribozyme.

In addition to the efficiency of the inactivation, the polyribozymes of the invention possess a number of advantages in comparison with known procedures:

The ribozymes function as enzymes, catalysing the cleavage of several viral RNAs specifically without modification of structure. This enzymatic cleavage leads to the destruction of all of the viral RNAs whereas the expression of the capsid protein which inhibits viral infection functions as an inhibitor of viral multiplication.

The ribozymes are non-coding RNA molecules which can not induce heteroencapsidations or generate new viral strains.

Whereas the specificity of the tolerance induced by the capsid protein is difficult to predict, ribozymes can be constructed in order to cleave specifically one or more viral strains, or several related viruses if the complementary arms correspond to the regions of homology conserved between the different strains or between the different related viruses.

In order to have a complete understanding of the invention, it will be useful to specify certain facts concerning ribozymes in general. A ribozyme is an RNA molecule which, by virtue of its sequence and secondary structure, possesses an endoribonuclease activity which enables it, when it hybridizes with a second molecule of complementary RNA, to cleave this second RNA. This latter is hence a "substrate" for the ribozyme.

The ribozyme has two essential parts:

(i) a sequence, which will be called "complementary sequence" in what follows, and which is selected so that, it is complementary to the substrate which it is desired to cleave, this enabling the two molecules to hybridize;

(ii) and a catalytic region which has a conserved sequence irrespective of the substrate selected and which does not take part in the hybridization with the substrate on account of its secondary structure which is in the form of a "loop".

Usually, the catalytic region is located within the complementary sequence, one part of the complementary sequence thus being situated at the 5' of the catalytic region and the other part at the 3'. These fragments of the complementary sequence on each side of the catalytic region are often called "hybridizing arms".

The object of the present invention is a polyribozyme. More particularly, it is a nucleic acid sequence, called "polyribozyme", which has an endoribonuclease activity and is capable of inactivating the gene for the capsid protein of a virus, characterized in that it comprises:

i) a sequence complementary to at least a part of the gene or its transcript or its replication intermediates and, included at distinct sites in this complementary sequence:

ii) a plurality of ribozyme catalytic regions;

iii) and, optionally, one or more sequences not complementary to the transcript of the said gene, the said non-complementary sequence(s) being inserted between 2 consecutive bases of the complementary sequence.

The term "polyribozyme" in the context of the present invention means an RNA molecule constituted by a head-to-tail series of ribozymes, the ribozyme thus being the unit motif of the polyribozyme. In other words, it is a series of catalytic regions connected together by hybridizing arms, the total length of these arms constituting the complementary sequence. The polyribozyme normally acts as a "unimolecule" against a single transcript, i.e. the cleavage sites of each of the catalytic regions are located on the same transcript: the capsid protein. The polyribozyme of the invention may also comprise, in addition to the 2 essential parts [(i), complementary sequence] and [(ii), catalytic regions] described above, one or more sequences (iii) non-complementary to the substrate. The nature and function of these non-complementary sequences will be described in detail hereafter.

Of the 2 essential parts of the polyribozyme, the complementary sequence is that which determines the substrate. In the case of the present invention, it is a sequence complementary to the gene for the capsid protein of a virus, or to a fragment of this gene. When the virus is an RNA (+) virus, the genes of which serve directly as mRNA, the complementary sequence is really complementary to the gene. In other cases, it is complementary to the transcript of the gene. It may also be complementary to a replication intermediate.

The complementary sequence may hybridize with the entire length of the capsid gene. In this case, the total length of the complementary sequence varies as a function of the length of the capsid gene in question. On the other hand, the complementary sequence may hybridize with only a fragment of the gene. The fragment in question must be long enough to allow the inclusion of at least two catalytic regions in the corresponding sequence of the polyribozyme. In general, the length of the complementary sequence, not counting the catalytic regions (i.e. the sum of the hybridizing arms), may vary from about 40 to 2000 bases. A length of 400 to 1000 is preferred, very many viruses having a gene for the capsid protein of about 1000 bases (for example, CMV, PLRV).

The term "complementary" in the context of the invention means a sufficiently high degree of complementarity to allow stable hybridization between the polyribozyme and this substrate, and the efficient cleavage of the substrate. When the polyribozyme does not contain a sequence of type (iii), i.e. "non-complementary", the degree of complementarity is usually 100%. The presence of a certain number of mismatches in the sequence, for example up to 10%, may be tolerated provided that that does not prevent the hybridization and cleavage of the substrate.

The (ii) part of the polyribozyme, i.e. the catalytic region, is derived from any type of suitable ribozyme, for example "hammer head", "hairpin" or "group I intron". One and the same polyribozyme may contain catalytic regions derived from different types of ribozymes, for example, "hammer head" and hairpin". Catalytic regions are preferably derived from ribozymes of the "hammer head" type, the consensus structure of which is illustrated in the FIGS. 1A, B, C and D. These ribozymes are described in detail in the patent application EP-A-321021 and WO-A-9119789.

Although the catalytic regions illustrated in FIG. 1 have a conserved structure and sequence, it has been observed that some nucleotides may be deleted, inserted, substituted or modified without prejudice to the activity of the ribozyme. The invention comprises the use of these modified catalytic regions in the polyribozyme provided that their catalytic activity is conserved. This activity can be verified by using the tests described below.

For example, one or more nucleotides of the catalytic region II illustrated in FIG. 1A may be replaced by nucleotides containing bases such as adenine, guanine, cytosine, methylcytosine, uracil, thymine, xanthine, hypoxanthine, inosine or other methylated bases. The "conserved" bases C–G which together form the first base pair of the catalytic loop, can be replaced by U-A (Koizumi et al., FEBS Letts. 228, 2, 228–230, 1988).

The nucleotides of the catalytic region illustrated in FIG. 1 can also be modified chemically. The nucleotides are composed of a base, a sugar and a monophosphate group. Each of these groups can thus be modified. Such modifications are described in "Principles of Nucleic Acid Structure" (Ed. Wolfram Sanger, Springer Verlag, N.Y., 1984). For example, the bases may bear substituents such as halogeno, hydroxy, amino, alkyl, azido, nitro, phenyl groups, etc. The sugar moiety of the nucleotide may also be subjected to modifications such as the replacement of the secondary hydroxyl groups by halogeno, amino or azido groups or even to 2' methylation.

The phosphate group of the nucleotides may be modified by the replacement of an oxygen by N, S or C, giving rise to a phosphoramidate, phosphorothioate and phosphonate, respectively. These latter may exhibit useful pharmacokinetic properties.

The bases and/or the nucleotides of the catalytic region may also bear substituents such as amino acids, for example, tyrosine or histidine.

It has also been observed that additional nucleotides may be inserted at certain sites of the catalytic region without prejudice to the activity of the ribozyme. For example, an additional base selected from among A, G, C or U may be inserted after $A^1$ in FIG. 1A or 1B.

Figure 1B:
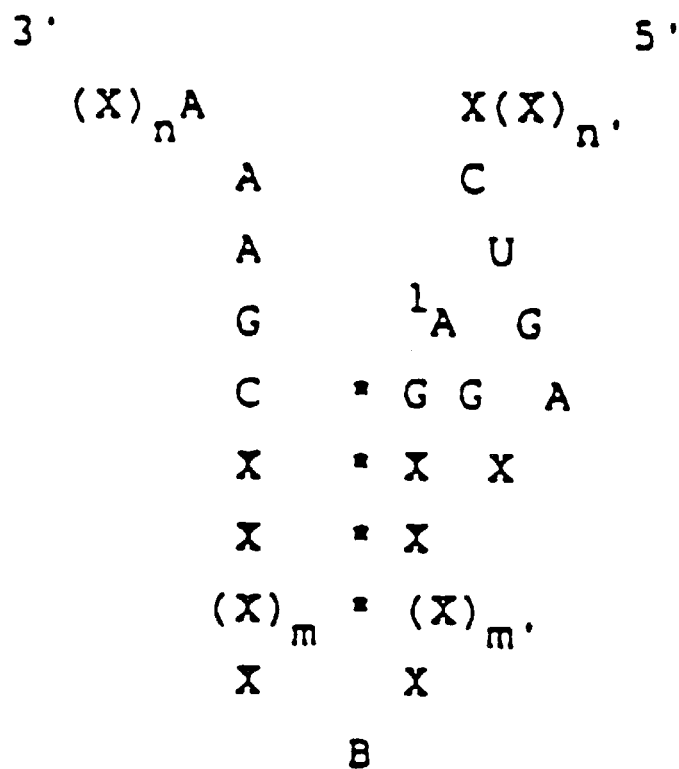
Figure 1C:
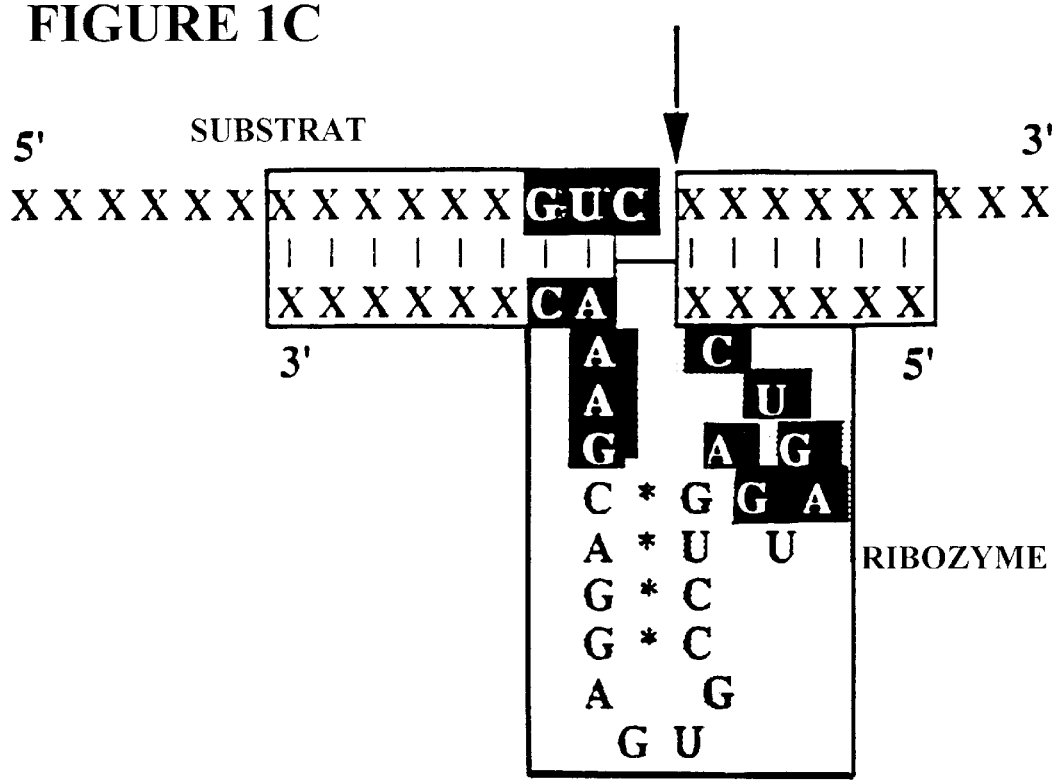
Figure 1D:
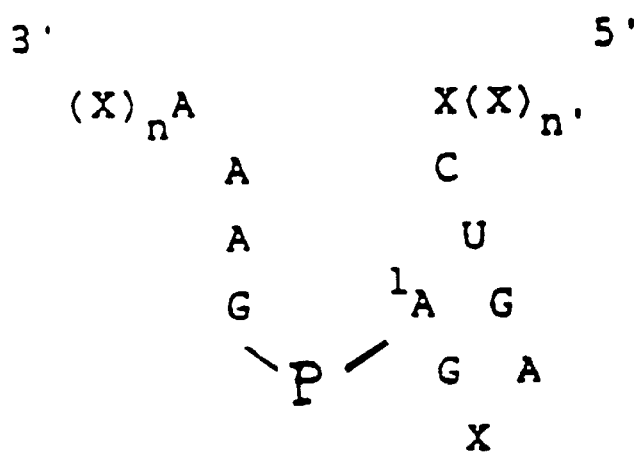

According to a variant of the invention, the ribozyme may comprise as catalytic region one or more structures such as those illustrated in FIG. 1D. This structure, called "minizyme", is described in the international patent application WO-A-9119789. It represents a catalytic region of the "hammerhead" type, the "loop" of which has been replaced by a "P" group. P may be a covalent link between G and $^1A$, one or more nucleotides (RNA or DNA, or a mixture, or even derivatives described above) or any atom or group of atoms other than a nucleotide which does not affect the catalytic activity. When P represents a plurality of nucleotides, it may contain internal base pairings. The sequence and the number of nucleotides constituting the group "P" is not critical and may vary from 1 to 20 nucleotides for example, and preferably from 1 to 6. It is preferable to select a sequence lacking internal base pairings of the Watson-Crick type.

The catalytic activity of the polyribozymes of the invention may be verified in vitro by placing the polyribozyme, or a sequence which after transcription will give rise to the polyribozyme, in contact with the substrate, followed by demonstration of the cleavage. The experimental conditions for the in vitro cleavage reaction are the following: a temperature comprised between 4 and 60° C., and preferably between 20 and 55° C., a pH comprised between about 7.0 and 9.0, in the presence of divalent metals, such as $Mg^{2+}$, at a concentration of 1 to 100 mM (preferably 1 to 20 mM). The polyribozyme is usually present in an equimolar ratio with the substrate, or in excess. The in vitro cleavage reactions are advantageously carried out according to the procedure described by Lamb and Hay (J. Gen. Virol., 1990, 71, 2257–2264). This article also describes suitable conditions for in vitro transcription for the production of ribozymes from oligodeoxyribonucleotides inserted into plasmids.

The in vivo cleavage conditions are those existing naturally in the cell.

The "hammerhead" ribozymes cleave the substrate immediately downstream from a "target" site XXX, preferably XUX, in which X represents one of the 4 bases A, C, G, U and U represents uracil. One particularly preferred target sequence is XUY in which Y represents A, C or U and X is often G, for example, GUC. Other target sites are possible, but less efficient, for example CAC, UAC and AAC. In the case of the ribozymes of the "hairpin" type, a preferred target sequence is AGUC.

These target sequences are important in the construction and functioning of the polyribozymes, not only because they indicate the positions of cleavage of the substrate but also because they define the position at which the catalytic region must be inserted in the complementary sequence. In fact, each catalytic region of the polyribozyme must be situated at a site in the complementary sequence which corresponds to a XUX site of the transcript. For example, if one XUX site is situated at position 108 of the gene for the capsid protein and another at position 205, a catalytic region is inserted at the corresponding position at 108 in the complementary sequence and another at 205.

The motif XUX is a motif which occurs very frequently in the RNA sequences. For example, on average there is a GUC motif every 64 bases in a sequence having a random and equal distribution of bases. This signifies that the substrate usually contains a plurality of XUX cleavage sites. As indicated above, the catalytic regions of the polyribozymes are situated at positions of the complementary sequence which correspond to the XUX sites. However, it is not necessary to include a catalytic region for each XUX target sequence of the substrate in order to obtain an efficient cleavage according to the invention. According to the invention, an efficient cleavage is obtained when the polyribozyme contains at least 2 catalytic regions. The total number of catalytic regions included in the complementary sequence is equal to or smaller than the total number of XUX sites present in the gene. The polyribozyme of the invention may thus contain a very variable number of catalytic regions. For example, in the case of CMV, the polyribozyme may contain from about 2 to about 11 or 12 catalytic regions, when the target sequence is GUC. In the case in which it is decided to include a smaller number of catalytic regions in the complementary sequence than the number of XUX sites in the substrate, the choice of the sites selected may be made by respecting the following criteria:

a) the distance between the 2 XUX sites targeted and, consequently, between 2 catalytic regions in the polyribozyme must be long enough to enable the hybridizing arms of the polyribozyme situated between the corresponding catalytic regions to hybridize with the substrate in a stable manner and to prevent the catalytic regions hybridizing with themselves. A distance of at least 8 bases, and preferably at least 14 bases, for example about 20 bases is particularly advantageous. Of course, this criterion must only be taken into consideration when the substrate contains XUX sites very close together. Otherwise, if the XUX sites of the substrate are separated from each other by more than 8 to 20 bases, this selection criterion is not important.

b) the XUX sites targeted are preferably situated in a part of the gene for the capsid protein which does not have significant secondary structure. This facilitates the access of the polyribozyme to the substrate and increases its efficacy.

c) the XUX sites targeted may form part of the regions of homology conserved between different strains of one and the same virus, or between different related viruses. The polyribozymes constructed by respecting this criterion may cleave specifically several viral strains or several related viruses. For example, the central region of the gene for the capsid protein of the PLRV is highly conserved compared with sequences of the capsid proteins of the related viruses BWYV and BYDV. The XUX sites, and particularly GUX within this central region, thus constitute preferred sites for a polyribozyme according to this variant of the invention.

Also, by way of example, the 5' end (over a length of about 100 bases) of the sequence of the capsid protein of the CMV is highly conserved between the strains I17F, FNY, M, I, O, Y, D and C. At position 84 within this conserved sequence there is a conserved GUC site in all of these strains.

According to this variant of the invention, a polyribozyme capable of inactivating several strains of the CMV comprises among its catalytic regions one catalytic region which is situated at the site of the complementary sequence corresponding to the position 84. (see examples hereafter).

d) another selection criterion of the XUX sites targeted is the absence of homology with endogenous genes of the plant to be transformed. In fact, although they are rare, some viruses possess sequences which find a homology in the genome of plants. It is thus important to avoid XUX sites situated within such a sequence.

According to a particularly preferred embodiment of the invention, the polyribozyme may comprise, in addition to the 2 essential parts (i) and (ii) described above, a 3rd constituent (iii) which is one or more sequences non-complementary to the gene for the capsid protein of the virus. Like the catalytic regions, these non-complementary sequences are inserted at distinct sites of the complementary sequence, the complementarity being interrupted by the insertion. Surprisingly, it was observed by the inventors that the presence of such non-complementary sequences within the hybridizing arms of the polyribozyme does not prevent the hybridization of the polyribozyme with the substrate, and in some cases can even improve the efficiency of the cleavage reaction.

These non-complementary sequences are inserted between 2 consecutive bases of the complementary sequence, the non-complementary sequence thus forming a colinear insertion with the complementary sequence. In this case, the polyribozyme has the structure:

((hybridizing arm-catalytic region-hybridizing arm)–(non-complementary sequence)$_n$)$_p$ in which n=0 or 1, and p>1.

As an example of this embodiment of the invention, mention may be made of a polyribozyme composed of a sequence of ribozymes, the hybridizing arms of which are complementary to distinct fragments, consecutive and adjoining, of the substrate and which are connected together by non-complementary sequences. In other words, the aggregate of the hybridizing arms in such a structure reconstitute the sequence complementary to the gene for the capsid protein.

The presence of non-complementary sequences in the polyribozyme signifies that the distance between two catalytic regions of the polyribozyme is greater than the distance between two corresponding GUC sites in the substrate. According to this variant of the invention, the length of the hybridizing arms located on each side of a catalytic region must be at least 4 bases, and preferably at least 8 bases on each side and may be as many as 800 to 1000 bases.

The nature of the non-complementary sequence(s) may be very variable depending on its (their) function. There may be sequences which have a "padding" function, i.e. which serve to increase the distance between two catalytic regions of the polyribozyme, when the corresponding two XUX sites of the substrate are relatively close to each other. In this manner, the formation of inactive duplexes between two neighbouring catalytic regions can be avoided. It is also possible to use as non-complementary sequences, sequences which have a defined secondary structure, which may have the effect of preventing a polyribozyme of considerable length, for example one with more than 800 bases, from refolding on itself in an inactive secondary structure. As an example of this type of structure, mention may be made of a ribozyme rendered inactive by the deletion of one or more essential bases. This mode of embodiment of the invention is exemplified by the polyribozyme 136 described in the examples below.

The non-complementary sequence of the polyribozyme may also have a precise function, for example, it may be constituted by a coding sequence which can be used to select transformants or also a sequence containing a ribozyme which acts on a substrate other than the capsid protein or which is cis acting on a part of the polyribozyme. Generally speaking, the non-complementary sequence does not code for a protein. It may also contain multisites for cloning. The non-complementary sequence usually has a length comprised between 2 and 500 bases, for example 20 to 100 bases. When there is a plurality of complementary sequences, they may together constitute up to about 90% of the length of the polyribozyme, for example 50%.

The polyribozyme of the invention is usually constituted of RNA. Nonetheless, it is possible to replace some parts of the polyribozyme by DNA, for example the hybridizing arms or parts of these arms, or also a part of the catalytic region, in particular the "loop", provided that the catalytic activity is maintained (see, for example, the substitution of the RNA by DNA described in the international patent application WO-9119789).

The polyribozyme of the invention can be constructed to inactivate any viral capsid protein. The capsid protein is the protein sub-unit, coded by the viral genome, which makes up the polymeric capsid. The capsid is composed of a succession of these identical protein sub-units which line-up along the nucleic acid. The spatial arrangement of the capsid sub-units gives rise to either a helicoidal or an icosahedric structure, according to the virus. The invention concerns polyribozymes directed to the capsid proteins of viruses having either helicoidal particles, or icosahedric particles, as well as those having an envelope. The envelope is a lipoprotein membrane surrounding the nucleocapsid.

As an example of a suitable virus, mention may be made of a virus selected from the following groups: the caulimoviruses, for example the Cauliflower Mosaic Virus (CaMV); the Geminiviruses, for example the Maize Streak Virus (MSV); the Reoviridae, for example the Wound Tumor Virus (WTV); the Rhabdoviridae, for example the Potato Yellow Dwarf Virus (PYDV), the Tomato Spotted Wilt Virus (TSWV); the Tobamoviruses, for example the Tobacco Mosaic Virus (TMV); the Potexviruses, for example the Potato Virus X (PVX); the Potyviruses, for example the Potato Virus Y (PVY); the Carlaviruses, for example the Carnation Latent Virus (CLV); the Closteroviruses, for example the Beet Yellow Virus (BYV); the Tobraviruses, for example the Tobacco Rattle Virus (TRV); the Hordei-viruses, for example the Barley Stripe Mosaic Virus; the Tymoviruses, for example the Turnip Yellow Mosaic virus (TYMV); the Luteoviruses, for example the Barley Yellow Dwarf Virus (BYDV) or the Potato Leaf Roll Virus (PLRV); the Tombusviruses, for example the Tomato Bushy Stunt Virus (TBSV); the Sobemoviruses, for example the Southern Bean Mosaic Virus (SBMV); the Tobacco Necrosis virus (TNV); the Nepoviruses, for example the Tobacco Ring Spot Virus (TRSV); the Comoviruses, for example the Cow Pea Mosaic Virus (CPMV); the Pea Enation Mosaic Virus (PEMV); the Cucumoviruses, for example the Cucumber Mosaic Virus (CMV); the Bromoviruses, for example the Brome Mosaic Virus (BMV); the Ilarviruses, for example the Tobacco Streak Virus (TSV). the sequences of these proteins are known (see for example the numerous literature references cited in the monograph: "Eléments de Virologie Végétale", Pierre Cornuet, I. N. R. A. Paris, 1987, ISBN: 2-85340-808-6).

According to a particularly preferred variant, the capsid protein is that of the Cucumber Mosaic Virus (CMV). The Cucumber Mosaic Virus is a virus belonging to the group of the Cucumoviruses which are of great agronomic importance since more than 750 species of plants may be infected by the CMV. The CMV is a multi-component virus composed of icosahedral particles containing three genomic RNAs (RNAs 1 to 3) and a subgenomic RNA (RNA 4). The RNA 3 contains a copy of the gene for the capsid protein; however, the subgenomic RNA4, which is derived from RNA 3, serves as matrix for the synthesis of the capsid protein. The different strains of CMV are divided into two groups:

the sub-group I which comprises the strains C, D, FNY, Y, I17F and Chi;

the sub-group II to which the strains Q and WL belong.

The comparison of the amino acid sequences of the capsid proteins of the CMV strains belonging to the same sub-group shows a homology of 95%. The sequence homologies between the sub-groups I and II are lower, of the order of 80%.

The polyribozymes of the invention directed against the capsid protein of the CMV (strain I17F) have been found to be extremely efficient in inactivating the different strains of the CMV, and have resulted in complete resistance of the transformed plants.

In addition to the polyribozymes, the invention also relates to a process for making a plant resistant to a virus, characterized by the introduction into the plant of a polyribozyme or a sequence coding for a polyribozyme such as described above.

Usually, the introduction of the polyribozyme into the plant is performed by genetic transformation, a DNA sequence coding for the polyribozyme thus being integrated stably into the genome of the plant.

All of the known means for introducing foreign DNA into plants may be used, for example Agrobacterium, electroporation, protoplast fusion, bombardment with a particle gun, or penetration of DNA into cells such as pollen, the microspore, the seed and the immature embryo, viral vectors such as the Geminiviruses or the satelite viruses. *Agrobacterium tumefaciens* and *rhizogenes* constitute the preferred means. In this case, the sequence coding for the polyribozyme is introduced into a suitable vector together with all of the regulatory sequences necessary such as promoters, terminators, etc. . . . as well as any sequence necessary for selecting the transformants.

The invention also relates to the transgenic plants obtained by the process. More particularly, it relates to transgenic plants resistant to a virus, characterized in that they contain in their genome a sequence which, after transcription, gives rise to a polyribozyme according to the invention .

In the context of the invention, the term "complete resistance" signifies a complete absence of symptoms; "tolerance" signifies that the plant is infected, i.e. it shows symptoms, but subsequently recovers. The term "sensitive" signifies that the plant exhibits symptoms and replicates the virus. The expression "resistant type" refers to the sum of the completely resistant plants and the tolerant plants.

The "resistant" nature of the transgenic plants of the invention can be tested in the following manner: a self-fertilization, or a cross with a non-transformed genotype, is carried out on a primary descendant to obtain $T_1$. Subsequently, $T_1$ plants is inoculated with the virus in question. According to the invention, after self-fertilization 75% of the $T_1$ are completely resistant. In the case of a cross with a non-transformed genotype, 50% of the plants are completely resistant (these figures are obtained, according to the invention, by testing a whole population of plants which had been subjected to a transformation and regeneration procedure. It is to be noted that only 75% of these plants are transformed).

The transformed nature of a plant can be verified by performing a "Southern blot" analysis and the expression of the sequence introduced by the transformation is verified by carrying out a "Northern blot" analysis. These analyses are described in the examples which follow.

The methods of transformation and regeneration of plants known in the prior art lend themselves perfectly to the production of transgenic plants protected by the polyribozyme of the invention. As an example, mention may be made of the method of transformation and regeneration of the melon described in the patent application No. EP-A-0412912.

The transgenic plants resistant to the CMV are particularly preferred, for example the melon, the cucumber, the courgette, the tomato, the pepper, the bean.

Various aspects of the invention are illustrated in the Figures:

FIGS. 1(A–D) shows the preferred structures of the catalytic regions of the polyribozyme of the invention, these regions being surrounded on each side by a sequence complementary to a part of the capsid protein of a virus:

(i) in FIG. 1A: X represents A, G, C or U; each X being identical or different; n+n'≧6, n and n' being identical or different; (*) represents a hydrogen bond between complementary ribonucleotides; X' and X" represent oligoribonucleotides which are complementary to each other over at least a part of their length and which may possibly be connected to each other by at least one nucleotide, thus forming a loop. An additional nucleotide selected from A, G, C or U may be inserted after A'. The catalytic region of the ribozyme is represented by part (II) of FIG. 1A, and the hybridizing arms by part (I).

(ii) in FIG. 1B: X, (*), n, n' and A' have the same meaning as in FIG. 1A. M and M'≧1 and are identical or different. B represents a bond, a base pair, a ribonucleotide or an oligoribonucleotide containing at least 2 ribonucleotides.

(iii) FIG. 1C SEQ. I.D. NO. 14 represents a preferred model of ribozymes (Haseloff and Gerlach, 1988) The RNA substrate may have any sequence (X) around the GUC cleavage site complementary to the ribozyme. The arrow indicates the cleavage site. The conserved bases are shown in black.

(iv) FIG. 1D represents the structure of a ribozyme (called "minizyme"), the loop of the catalytic region of which is replaced by an element "P". P may be at least 1 nucleotide (ribonucleotides, deoxyribo-nucleotides, derivatives or a mixture), provided that the ribonucleotides of the "P" group are not base paired by "Watson-Crick" base pairings when the sequences $(X')_n$ and $(X)_{n'}$ and P are constituted exclusively of ribonucleotides. "P" may also be a bond or any atom or group of atoms which do not affect the catalytic activity of the ribozyme. X has the same meaning as FIG. 1A.

FIG. 2 shows the sequence of the capsid protein of the CMV (I7F)SEQ. I.D. NO. 5, the GUC sites being underlined.

FIG. 3 presents the structures of the oligodeoxyribonucleotides A SEQ. I.D. NO. 6; SEQ. I.D. NO. 7, B SEQ. I.D. NO. 8; SEQ. I.D. NO. 9, C SEQ. I.D. NO. 10; SEQ. I.D. NO. 11, E SEQ. I.D. NO. 12; SEQ. I.D. NO. 13, used for the directed mutagenesis experiments for the purpose of introducing the catalytic site of the TobRSV at different sites in the sequence of the capsid protein of the CMV (shown hybridized with the DNA matrix sequence).

FIG. 4 illustrates the structure of the genes constructed in order to induce resistance to the CMV:

(i) capsid protein (ii) polyribozyme 136: sequence complementary to the capsid protein bearing 2 ribozymes;

(iii) polyribozyme 161: sequence complementary to the capsid protein bearing 3 ribozymes;

(iv) polyribozyme 163: fragment complementary to the capsid protein bearing 3 ribozymes;

(v) polyribozyme 165: sequence complementary to the capsid protein bearing 4 ribozymes;

FIG. 5 shows the Northern blot analysis of the transgenic melon plants (primary transformants, T1 and T2 descendants in some cases) expressing the polyribozyme 136:

T0: primary transformant;

T1: T1 descendant;

T2: T2 descendant;

A: line 141.1;

NT: untransformed control.

FIG. 6 shows the Southern analysis of the transgenic melon plants (primary transformants, T1 and T2 descendants in some cases) expressing the polyribozyme 136:

T0: primary transformant;

T1: T1 descendant;

T2: T2 descendant;

NT: untransformed control

FIG. 7 shows the Southern blot analysis of the transgenic melon plants (primary transformants, T1 and T2 descendants in some cases) expressing the gene for the capsid protein:

T0: primary transformant;

T1: T1 descendant;

T2: T2 descendant;

A: line 88.105;

B: line 159.8

NT: untransformed control.

FIG. 8 shows the Western blot analysis of the transgenic melon plants (primary transformants) transformed by pBIOS135:

A, B, C, D and E: primary transformants of 5 lines;

NT: untransformed control;

R: reconstruction with 20 ng of CMV.

FIG. 9 shows the development of the symptoms of the CMV with time in the lines transformed by pBIOS 135:

D: day;

▮: plants without symptoms

▒: tolerant plants

: sensitive plants.

FIG. 10 shows the development of the symptoms of the CMV with time in the lines transformed by pBIOS 135:

D: day;

▮: plants without symptoms

▒: tolerant plants

: sensitive plants.

EXAMPLES

The following examples describe the construction of 4 polyribozymes containing 3 or 4 ribozymes composed of the Hammerhead consensus structure of 24 bases (FIG. 1) and arms complementary to the sequence of the capsid protein of the CMV (I17F strain) of different sizes. The numbering of the nucleotide sequence of the capsid protein shown in these examples corresponds to those used in the patent application EP-A-0412912.

Each of these ribozymes cleaves a different GUC sequence along the sequence of the gene for the capsid protein of the CMV. The structure of these constructs is illustrated in FIG. 4:

The polyribozyme 136, 1074 bases long, contains the ribozymes A (position 84) and B (position 108) and the ribozyme C* (position 204), from which a G and an A (positions 20 and 21) have been deleted, the ribozymes being surrounded by complementary arms of the following lengths:

82 nucleotides from the 5' end to the ribozyme A;

22 nucleotides between the ribozymes A and B;

94 nucleotides between the ribozymes B and C*;

and 803 nucleotides from the ribozyme C* to the 3' end.

The polyribozyme 161, 1076 bases long, is identical with the polyribozyme 136, the only difference being that the ribozyme C at position 204 possesses the G and the A deleted in the ribozyme C*.

The polyribozyme 163, 426 nucleotides long, contains the 3 ribozymes A (position 84), B (position 108) and C (position 204) surrounded by complementary arms of the following lengths:

82 nucleotides from the 5' end to the ribozyme A;

22 nucleotides between the ribozymes A and B;

94 nucleotides between the ribozymes B and C;

and 153 nucleotides from the ribozyme C to the 3' end.

The polykibozyme 165, 1099 nucleotides long, contains the 4 ribozymes A (position 84), B (position 108), C (position 204) and E (position 608) which are surrounded by complementary arms of the following lengths:

82 nucleotides from the 5' end to the ribozyme A;

22 nucleotides between the ribozymes A and B;

94 nucleotides between the ribozymes C and E;

399 nucleotides from the ribozyme E to the 3' end.

The polyribozymes do not contain the signals necessary for their expression and integration into the genome of the plants. A constitutive or non-constitutive promoter (for example a viral or bacterial promoter such as NOS, or a plant promoter such as that for Rubisco or that for ubiquitin) must be placed at the 5' end of the polyribozyme and a poly(A) sequence must be placed at the 3' end. Several promoters which function in plants can be used; the inventors selected the 35S promoter derived from the Cauliflower Mosaic polymerase. The following four oligonucleotides were ordered from the EUROGENTEC company:

```
Oligo A:
5' TCGACGGTTACCTGATGAGTCCGTGAGGACGAAACCAGCACTGGTTG 3'   (SEQ. ID. NO:1)

Oligo B:
5' CGGGAACCACCTGATGAGTCCGTGAGGACGAAACGCGGACGACG 3'     (SEQ. ID. NO:2)

Oligo C:
5' GTTAATAGTTGCTGATGAGTCCGTGAGGACGAAACGACCAGCTGC 3'    (SEQ. ID. NO:3)

Oligo E:
5' GAATACACGAGCTGATGAGTCCGTGAGGACGAAACGGCGTACTTTC 3'   (SEQ. ID. NO:4)
```

Virus (CaMV), reputed to be the strongest constitutive promoter. The polyadenylation signal poly (A) may be that of the 35S gene of the CaMV, that of genes isolated from plants or of octopine synthase; the inventors selected the poly (A) signal derived from the gene for nopaline synthase (tnos). The expression cassettes constructed were introduced in the pBIOS 4 transformation vector derived from the pBI 121 vector containing the gene for resistance to kanamycin (gene neo which codes for neomycin phospho-transferase) and the iud A gene which codes for glucuronidase. The protocol for the genetic transformation of melon cotyledons and the regeneration of transgenic melon plants is identical with that described in the patent "transgenic melon", No. EP-A-0412912 in the name of BIOSEM.

Example 1

Construction of a Ribosome Directed Against the Gene for the Capsid Protein of the Cucumber Mosaic Virus, Strain I17F The phagemid bluescribe pBSIISK (STRATAGENE) containing the DNA complementary to the RNA4 of the CMVstrain I17F called pBIOS 113, the procedure for the production of which is described in the European patent application EP-A-0412912, served as starting point for the construction of the different ribozymes used to obtain transgenic melons resistant to different strains of CMV.

The catalytic site of the satellite TobRV (Tobacco Ringspot Virus) was introduced at different positions in the sequence of the gene for the capsid protein. The sequence of the DNA complementary to the RNA4 of the CMV strain I17F, 1007 base pairs long, is shown in FIG. 3 of EP-A-0412912; the part coding for the capsid protein is shown with the amino acid sequence.

As the ribozyme of the "Hammerhead" type described by Haselhoff and Gerlach cleaves preferentially after the C of the GUC motifs, 4 positions on the sequence coding for the capsid protein were selected (FIG. 2):

position A, nucleotide 84,
position B, nucleotide 108,
position C, nucleotide 204,
position E, nucleotide 608.

In order to introduce the 24 bases of the ribozyme commonly called "hammerhead" at these positions, it was decided to use the method of mutagenesis on single-stranded DNA developed by KUNKEL (Proc. Nat. Acad. Sci. 82:488–492) which requires synthetic oligodeoxyribonucleotides which hybridize partially with the DNA that is to be mutagenised and which serve as primer at the 3' end for the synthesis of a complementary strand using a DNA With the aid of these 4 oligonucleotides and the directed mutagenesis kit purchased from the BIORAD company (catalogue number 170-3576) single stranded DNA produced from the phagemid pBIOS 113 was mutagenised. FIG. 3 shows the hybridization of the 4 oligonucleotides to the target single stranded DNA and the arrows indicate the action of the DNA polymerase which synthesizes the complementary strand. The analysis of the few recombinant clones obtained after transformation of *E. coli* was first made by digestion with restriction enzymes in order to detect a size increase of some of the fragments. One of the clones, pBIOS 116, which apparently contained 3 catalytic sites was sequenced with the aid of the "sequenase R" kit version II obtained from the United States Biochemicals company by using an oligonucleotide of 22 bases, oligo No.13 (position 53 to 74). The results showed the perfect insertion of the catalytic sites A and B and the imperfect insertion of the catalytic site C. A deletion of the two bases at positions 20 and 21 (G and A) of the catalytic site had taken place. Although this site cannot be functional for cleavage, as demonstrated by Lamb and Hay (Journal of General Virology, 1990, 71:2257–2264), it was decided to clone the DNA fragment of about 1100 bp (1007 bp+21 bp×2+19 bp+adjacent sequences of the polylinkers at 5' and 3') in opposite orientations in the expression vector pBIOS 3 (Perez et al., Plant Mol. Biology 1989, 13:365–373), in order to study the effect of the presence of non-complementary sequences lacking ribozymic activity in the polyribozyme. For that purpose the KpnI-XbaI fragment of pBIOS 113 was cloned at the KpnI-XbaI sites of the plasmid pGEH7 2f (+) obtained from the PROMEGA BIOTECH company; this was done for the purpose of having BamHI sites on either side of the sequence for the capsid protein containing the catalytic sites. The resulting plasmid pBIOS 151 was then digested by BamHI and the fragment under consideration (polyribozyme 136, FIG. 4) was introduced into the BamHI site of PBIOS 3. A recombinant clone containing the fragment in the anti-sense orientation, under the control of the strong constitutive promoter of the Cauliflower Mosaic Virus and the terminator of the gene for nopaline synthase, was selected and called pBIOS 125.

The EcoRI fragment of this plasmid containing the ribozyme (complementary fragment with two functional catalytic sites and one deleted), under the control of sequences for transcriptional regulation mentioned above, was cloned at the EcoRI site of the binary vector pBIOS 4. The latter is a derivative of the vector pBI 121 (Jefferson et al., 1987: EMBO Journal 6:3901–3907) which was modified by the suppression of the EcoRI site situated at the 3' end of the gene coding for beta-glucuronidase and the creation of a EcoRI site situated at the 5' end of the same gene. The resulting binary vector, pBIOS 136, was used in different transformation experiments after triparental conjugation in the disarmed strain of *Agrobacterium tumefaciens* RC58'3, which is derived from the strain C58'3 (Mullineaux et al., Plant Science 63:237–245, 1989) and is in fact a spontaneous mutant resistant to rifampicin.

Example 2

Construction of Differents Ribozymes Directed Against the Gene for the Capsid Protein of the Cucumber Mosaic Virus, Strain I17F Given that the polyribozyme 136 (FIG. 4) described in Example 1 did not contain the catalytic site directed against position 608 and that the one directed against position 204 was incomplete, further directed mutagenesis experiments were initiated. To this end, the EcoRI fragment of the plasmid was cloned in the phage M13 mp18 digested by EcoRI, obtained from the PHARMACIA company. A recombinant phage allowing the encapsidation of the coding strand of the gene for the capsid protein containing the two correct catalytic sites was characterised and it was used as matrix for the new mutagenesis experiments utilizing the oligodeoxyribonucleotides C and E (together or separately). These latter were conducted like those presented in the previous example, except that the yield of single stranded matrix is much more favourable since the starting material was a phage. Different recombinant clones were sequenced by using the oligonucleotide No.13 and a 19-mer oligonucleotide (position 694 to position 676), this latter making it possible to sequence the catalytic site introduced at position 608. The clones containing catalytic sites in conformity with the invention were used for the construction of the binary vectors pBIOS 161, pBIOS 163 and pBIOS 165 (see FIG. 4). The binary vector pBIOS 161 is identical with pBIOS 136 except that pBIOS 161 contains the catalytic site C undeleted, In the case of genes coding for the ribozymes which hybridize with the entire sequence of the gene for the capsid protein and containing three functional catalytic sites A, B, C (the case for pBIOS 161) or four functional catalytic sites A, B, C, E (the case for pBIOS 165), cloning at the EcoRI site of the binary vector pBIOS 4 is carried out directly after purification of the EcoRI fragment comprising the 35S promoter, the ribozyme, the terminator NOS. In the case of the ribozyme which contains 3 catalytic sites A, B, C and hybridizes with only the first 360 bases at the 5' end of the RNA4 of the C4V (the case for pBIOS 163), a deletion of the remaining 3' part was made after digestion with the restriction enzyme HindIII (positions 361 in the sequence of the gene for the capsid protein and of the HindIII site situated at the 3' border of this sequence and resulting from a polylinker). The thus deleted EcoRI fragment of the plasmid was then cloned at the EcoRI site of the binary vector pBIOS 4.

Transformation and Regeneration of Melons Expressing the Polyribozymes

The last 3 binary vectors were introduced into Agrobacterium and used for transformation as described in the patent application EP-A-0412912.

Example 3

Figure 5:
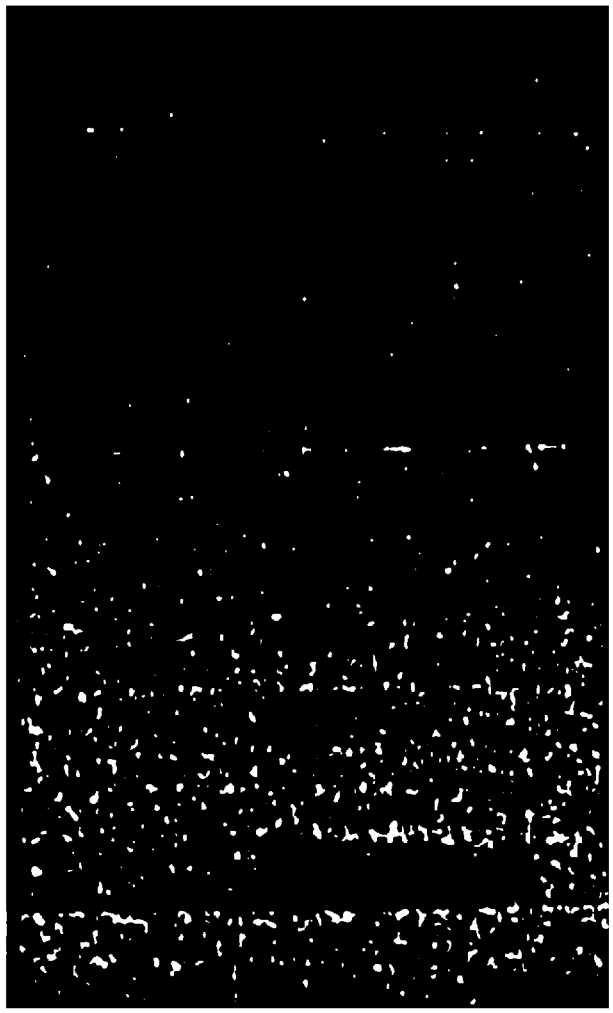

Molecular Analysis of the Transgenic Plants
Northern Blot Analyses:

The melon plants obtained after transformation with pBIOS 136 were analysed by means of Northern blot (FIG. 5). The total RNAs were extracted from young leaves of transgenic and non-transgenic plants cultivated in a greenhouse, according to the protocol of Chandler et al. (Plant Physiology (1983) 74:47–54).

They were subjected to electrophoresis in a 1% denaturing agarose gel, transferred to Hybond C and hybridized with the probe constituted by the fragments resulting from a triple digestion of the BamHI fragment, which corresponds to the complete complementary fragment of the gene for the capsid protein, bearing the 3 ribozymes, two of which are functional (polyribozyme 136). The triple digestion favours hybridization between the homologous sequences and makes it possible to obtain a more intense signal.

The homogeneity of the quantities of total RNAs loaded on to the gel and the quality of the RNAs were verified by staining of the membrane with methylene blue. The results obtained at the transcriptional level for the primary transformants and the corresponding T1 and T2 descendants are illustrated in FIG. 2 and show that:

- a major transcript of 1.45 kb is observed in all of the samples derived from transformed plants but not in the negative control;
- the number of transcripts varies considerably according to the primary transformants. This may be explained by integrations of the T-DNA or fragments of T-DNA at different loci of the plant genome and thus by environmental effects:
- no correlation exists between the transcriptional levels of the primary transformants and those of their T1 and T2 descendants.

Southern Blot Analyses

The melon plants obtained after transformation with pBIOS 136 or pBIOS 135 were analysed by means of Southern blot (FIGS. 6 and 7). The total DNAs were extracted from young leaves of transgenic (primary transformants, T1 and T2 descendants in some cases) and non-transgenic plants cultivated in a greenhouse, according to the protocol of Dellaporta et al. (Plant Molecular Biology Reporter (1983) 1:19–21). They were hydrolysed by EcoRI (cloning site of the expression cassette of the gene of interest in pBIOS4), subjected to electrophoresis in 0.8% agarose gel, transferred to Hybond N+ and hybridized with the three probes, gene npt II, polyribozyme 136 triply digested (cf. Northern blot analysis) and gene gus.

The results obtained for 5 transformation events with PBIOS 136 (FIG. 6) show that:

Lines 146.42:

In the case of the primary transformant 146.42, its T1 descendant and two T2 descendants, the hybridization profiles with the 3 probes are identical, which indicates that there has been no segregation of the fragments of the T-DNA and that there is probably a single locus The polyribozyme 136 is present in the plant genome in several copies. In fact, 4 hybridization bands with sizes of 1.75 kb; 4.4 kb; 8.3 kb and 8.8 kb are visible. The 1.75 kb band corresponds to the theoretical size of the band expected with the couple (EcoRI, polyribozyme). The 4.4 kb band hybridizes with both the polyribozyme 136 and the gene npt II. Furthermore, the analysis with the EcoRI/npt II couple does not lead to the detection of this band, which indicates the presence of a single copy of the npt II gene in the plant genome. The bands of 8.3 kb and 8.8 kb hybridize with the polyribozyme 136 and the gus gene. Only these two bands are detected by the EcoRI/gus couple, which reveals the presence of two copies of all or part of the gus gene. The hybridization of the 3 probes with DNA of the T0, T1 and T2 plants digested with XbaI also suggests the presence of a single locus.

Lines 146.34:

In the case of the primary transformant 146.34 and its T1 descendant, only some of the hybridization bands of the primary transformant subsist in the individual T1, which emphasizes the fact that certain fragments of the T-DNA have been eliminated. For the analysis of the EcoRI/polyribozyme 136, 3 bands with sizes of 1.75 kb, 3 kb and 5.3 kb are common to the T0 and T1 plants and 3 additional bands with sizes of 7.3 kb, 6.8 kb and 4.25 kb characterize the plant T0. This indicates the presence of at least 3 and 6 copies of the polyribozyme 136 in the T1 and T0 plants, respectively. In npt II hybridization, the two EcoRI bands of 3 kb and 5.3 kb are detected in the T0 plants, which shows the presence of two copies of all or part of the npt II gene. Only the EcoRI band of 3 kb is visible in the T1 plant, which indicates the presence of a single copy of the npt II gene. In gus hybridization, the 3 EcoRI bands with sizes of 4.25 kb, 5.3 kb and 6.8 kb are found in the T0 plant whereas only the band of 5.3 kb is present in the T1 descendant. This reveals the presence of 3 copies and one copy of all or part of the gus gene in the T0 and T1 plants, respectively. Moreover, the hybridization of the 3 probes with the DNAs of the T0 and T1 plants digested by XbaI suggests the existence of 2 loci.

Lines 146.30 and 146.28:

In the case of the primary transformants 146.30 and 146.28 as well as their respective T1 descendants similar observations are made.

Line 141.1:

In the case of the primary transformant 141.1 and its descendant, the hybridization profiles are similar. EcoRI bands of 1.75 kb, 10 kb and 10 kb are revealed with the probes polyribozyme 136, npt II and gus, respectively. This shows the presence of a single copy of the T-DNA integrated into the plant genome.

In conclusion, genetic stability is observed in the case of the transformant 146.42 and its descendants (T1 and T2) and in that of the transformant 141.1 and its descendant T1. A high number of copies of the T-DNA or fragments of the T-DNA characterise 4 of the lines studied whereas the line 141.1 possesses only one integrated copy of the T-DNA.

Moreover, the presence of a copy of the T-DNA and/or part of the T-DNA is also to be noted in the lines transformed with pBIOS 135 (FIG. 7).

Western Blot Analysis (Comparative Analysis)

Figure 8:
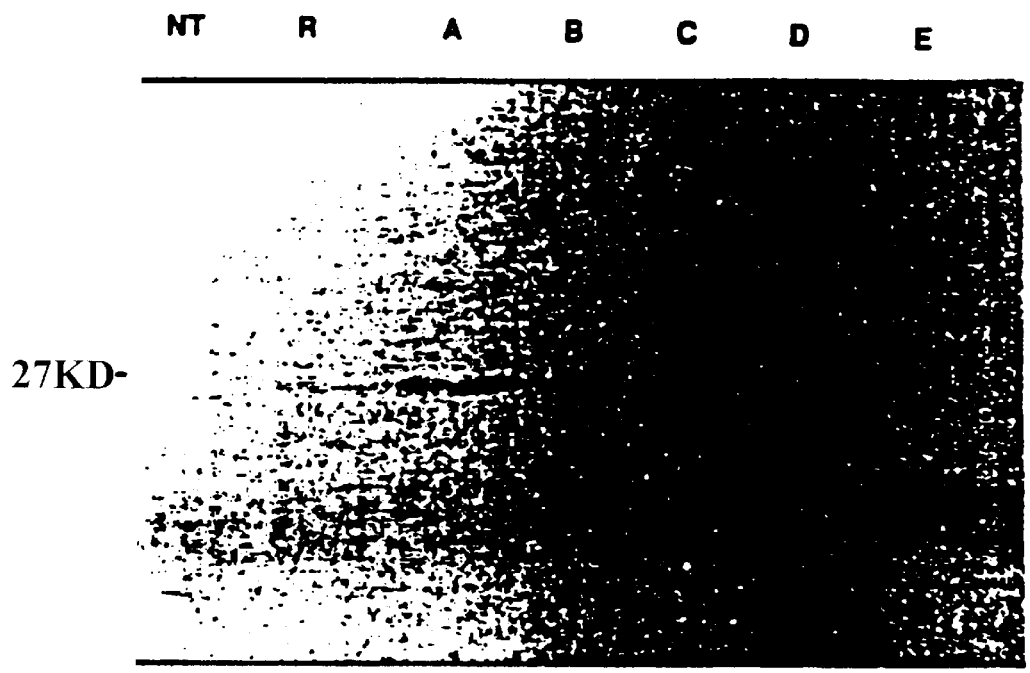

The transgenic melon plants transformed with pBIOS 4 containing the expression cassette of the gene for the capsid protein were analysed by means of Western blot. The patent application EP-A-0412912 of the 11.08.1989 in the name of BIOSEM recounts the methodology employed and the results obtained. However, it should be emphasized that the level of expression of the gene for the capsid protein varies between 0.001% and 0.4% of the total proteins. By means of a few examples, FIG. 8 illustrates this variation in the level of expression, which depends on the age of the leaf and probably on environmental effects on the plant genome.

Example 4

Tests of Resistance of the Melons Transformed by the Polyribozyme 136 and the Capsid Protein to the CMV (COMPARATIVE TEST)

The transgenic melon plants (genotype TEZIER 10) which express the gene for the capsid protein or the polyribozyme 136 were self-fertilized or crossed with untransformed plants of the genotype TEZIER 10. The seeds derived from these self-fertilizations (T1 generation) and subsequent self-fertilizations (generation T2, . . . ) were sown in a phytotron (climatised chamber with a 16 hour light period).

At the 2 to 4 leaves stage, 23 plants originating from the descendants were mechanically inoculated with a powdered preparation of fresh leaves infected with the CMV strain TL28.

After 16 days of infection (optimal period), the symptoms (mosaic, pleating of the leaf blade, yellowing) were evaluated. The infected plants are classified in three category;

resistant plants (R) which have no symptoms;

sensitive plants (S) which have symptoms;

tolerant plants (T) which are the plants which "recover", i.e. the nascent leaves develop without symptoms whereas the old leaves exhibit symptoms.

Several cycles of "recovery" may occur. Whether or not nascent healthy leaves change into infected leaves depends on the climatic conditions.

The "resistant-type" plants include both the plants without symptoms and tolerant plants.

The controls used in the test of resistance to CMV are:

sensitive controls: TEZIER 10 and Vedrantais;

resistant controls which possess at least three recessive genes of the CMV, Virgos and Free Cucumber.

Resistance of Melon Lines in Generation T1 Which Express the Gene for the Capsid Protein to the CMV Strain TL 28:

The results obtained for 20 lines are given in Table 1 and show that:

The infection with TL 28 leads to the production of 3 to 30% of TI plants without symptoms. The untransformed control TEZIER 10, inoculated with TL 28 yields 0% of plants without symptoms. The resistant controls Virgos and Free Cucumber give rise to 92 and 100% of plants without symptoms, respectively, and do not show any tolerance phenomenon.

The phenomenon of recovery exists in a high proportion of cases. Fourteen lines studied show a not insignificant percentage (22 to 59%) of tolerant T1 plants.

There is no correlation between the percentage of resistant and tolerant T1 plants and the level of expression of the capsid protein. In fact, the lines 159.8 and 164.2, for example, which have an identical level of expression of the capsid protein (0.01%) exhibit different levels of resistance. The T1 individuals of the 159.8 line are all sensitive whereas in the 164.2 line 26% are without symptoms and 48% are tolerant.

Most of the lines expressing the gene for the capsid protein were obtained by self-fertilization. The expected theoretical frequency of the gene for the capsid protein is 75% in the T1 plants inoculated with the CMV. The percentage of resistant-type plants (without symptoms and tolerant) vary between 25 and 82% depending on the transgenic lines.

TABLE 1

RESISTANCE OF T1 GENERATION MELON PLANTS WHICH EXPRESS THE GENE FOR THE CAPSID PROTEIN TO THE CMV STRAIN TL28

| LINES | CROSS | % CP | % R | % T | % S |
|---|---|---|---|---|---|
| 88.105 | I | 0.01 | 3 | 22 | 75 |
| 131.6 | BC | 0.06 | 9 | 0 | 81 |
| 145.1 | I | | 4 | 0 | 96 |
| 145.2 | BC | 0.06 | 22 | 35 | 43 |
| 153.4 | I | 0.1 | 0 | 30 | 70 |
| 153.5 | I | 0.06 | 17 | 57 | 26 |
| 153.6 | I | 0.13 | 18 | 32 | 50 |
| 153.8 | I | 0.01 | 17 | 43 | 40 |

TABLE 1-continued

RESISTANCE OF T1 GENERATION MELON PLANTS
WHICH EXPRESS THE GENE FOR
THE CAPSID PROTEIN TO THE CMV STRAIN TL28

| LINES | CROSS | % CP | % R | % T | % S |
|---|---|---|---|---|---|
| 153.9 | I | 0.06 | 30 | 39 | 31 |
| 153.19 | I | 0.05 | 29 | 52 | 19 |
| 153.20 | I | 0.01 | 30 | 39 | 31 |
| 153.22 | I | 0.4 | 18 | 27 | 55 |
| 159.4 | BC | 0.002 | 0 | 0 | 100 |
| 159.8 | I | 0.01 | 0 | 0 | 100 |
| 164.2 | I | 0.01 | 26 | 48 | 26 |
| 164.23 | BC | 0.01 | 30 | 35 | 35 |
| 166.5 | I | | 23 | 55 | 22 |
| 166.10 | I | | 23 | 59 | 18 |
| 170.5 | BC | 0.3 | 9 | 0 | 91 |
| 171.7 | I | | 9 | 0 | 91 |
| TEZIER 10 | | | 0 | 0 | 100 |
| VEDRANTAIS | | | 0 | 0 | 100 |
| VIRGOS | | | 92 | 0 | 8 |
| FREE CUCUMBER | | | 100 | 0 | 0 |

TABLE 2

RESISTANCE OF T1 GENERATION MELON PLANTS
WHICH EXPRESS THE POLYRIBOZYME
136 TO THE CMV STRAIN TL28

| LINES | CROSS | % R | % T | % S |
|---|---|---|---|---|
| 141.1 | BC | 48 | 9 | 43 |
| 141.2 | BC | 39 | 26 | 35 |
| 141.3 | BC | 43 | 17 | 40 |
| 141.4 | BC | 26 | 26 | 48 |
| 141.5 | BC | 52 | 0 | 48 |
| 141.6 | BC | 39 | 0 | 61 |
| 146.19 | BC | 30 | 0 | 70 |
| 146.28 | BC | 47 | 0 | 53 |
| 146.42 | I | 87 | 0 | 13 |
| 146.47 | BC | 43 | 0 | 57 |
| TEZIER 10 | | 0 | 0 | 100 |
| VEDRANTAIS | | 0 | 0 | 100 |
| VIRGOS | | 92 | 0 | 8 |
| FREE CUCUMBER | | 100 | 0 | 0 |

Legend:

I: self-fertilization

BC: cross with the untransformed genotype TEZIER 10

% CP: level of expression of the capsid protein as percentage of the soluble total proteins % R: percentage of resistant plants or plants without symptoms % T: percentage of tolerant plants % S: percentage of sensitive plants Resistance of Melon Lines in Generation T1 Which Express the Polyribozyme 136 to the CMV Strain TL 28:

The results obtained for 13 lines are given in Table 2 and show that:

in the case of 10 lines, 30 to 87% of the T1 individuals are without symptoms after infection with TL 28;

the "recovery" phenomenon is scarcely present. Only 4 lines show tolerant T1 plants, to the extent of 9 to 26%.

Most of the lines expressing the polyribozyme 136 were obtained by crosses with the untransformed line TZ 10. The expected theoretical frequency of the polyribozyme is 50% in the T1 plants inoculated with the CMV. The percentage of "resistant-type" plants varies between 30 and 65% depending on the transgenic lines.

In conclusion, in the case of the "ribozyme" strategy, a larger number of lines of the T1 generation are without symptoms and possess very few tolerant plants.

Legend:

I: self-fertilization

BC: cross with the untransformed genotype TEZIER 10

% R: percentage of resistant plants or plants without symptoms

% T: percentage of tolerant plants

% S: percentage of sensitive plants

Summary of the Tests of Resistance to the CMV Strain TL 28 and of the Evaluation of Segregation by Means of the GUS Test for Certain Lines:

The results presented in Table 3 show:

the production of two lines of the resistant type (plants without symptoms and tolerant plants) which express the gene for the capsid protein (lines 88.105 and 153.8) and one completely resistant line (plants without symptoms) which expresses the polyribozyme 136 (line 146.42).

the production of two tolerant lines (tolerant plants) which express the polyribozyme 136 (lines 141.1 and 146.28).

TABLE 3

TEST OF RESISTANCE TO THE CMV STRAIN TL28 AND BEHAVIOURS
OF THE GUS GENE AND THE GENE FOR RESISTANCE IN THE
DESCENDANTS

| LINES | X | GEN | MOLEC. CHARACT. | % G | R | | | T | | | S | | |
|---|---|---|---|---|---|---|---|---|---|---|---|---|---|
| | | | | | % R | % G | QT. VIRUS | % R | % G | QT. VIRUS | % R | % G | QT. VIRUS |
| 88.105 | | T0 | K.CP.G. | | | | | | | | | | |
| 702 | I | T1 | K.CP.G. | 80 | 3 | 100 | 0.78 +/− 0.02 | 22 | 100 | 1.46 +/− 0.39 | 75 | 53 | 1.42 +/− 0.25 |
| 710 | I | T2 | K.CP.G. | 100 | | | | 100 | 100 | 0.71 +/− 0.11 | | | |

TABLE 3-continued

TEST OF RESISTANCE TO THE CMV STRAIN TL28 AND BEHAVIOURS
OF THE GUS GENE AND THE GENE FOR RESISTANCE IN THE
DESCENDANTS

| LINES | X | GEN | MOLEC. CHARACT. | % G | R % R | % G | QT. VIRUS | T % R | % G | QT. VIRUS | S % R | % G | QT. VIRUS |
|---|---|---|---|---|---|---|---|---|---|---|---|---|---|
| 153.8 | | T0 | K.CP.G. | | | | | | | | | | |
| 740 | I | T1 | K.CP.G. | 73 | 12 | 100 | 0.56 +/− 0.10 | 43 | 100 | 0.85 +/− 0.10 | 45 | 55 | 0.94 +/− 0.17 |
| 545 | I | T2 | K.CP.G. | 100 | 50 | 100 | 0.69 +/− 0.56 | 50 | 100 | 0.92 +/− 0.57 | | | |
| 159.8 | | T0 | K.CP.G. | | | | | | | | | | |
| 739.1 | I | T1 | K.CP.G. | 0 | | | | | | | 100 | 0 | 1.42 +/− 0.27 |
| 141.1 | | T0 | K.RZ.G. | | | | | | | | | | |
| 730.1 | BC | T1 | K.RZ.G. | 57 | | | | 40 | 100 | 0.88 +/− 0.21 | 60 | 19 | 1.05 +/− 0.17 |
| 146.28 | | T0 | K.RZ.G. | | | | | | | | | | |
| 734.1 | BC | T1 | K.RZ.G. | 73 | | | | | | | 100 | 73 | 1.96 +/− 0.46 |
| 539.2 | I | T2 | K.RZ.G. | 68 | | | | 37 | 100 | 1.00 +/− 0.25 | 63 | 53 | 1.64 +/− 0.42 |
| 146.31 | | T0 | K.RZ.G | | | | | | | | | | |
| 735.1 | BC | T1 | K.RZ.G | 0 | | | | | | | 100 | 0 | 1.64 +/− 0.46 |
| 146.42 | | T0 | K.RZ.G. | | | | | | | | | | |
| 755.1 | I | T1 | K.RZ.G. | 77 | 79 | 100 | 0.42 +/− 0.22 | | | | 21 | 0 | 1.75 +/− 0.37 |
| 540 | I | T2 | K.RZ.G. | 82 | 90 | 100 | 0.45 +/− 0.30 | | | | 10 | 0 | 1.52 +/− 0.65 |
| TEZIER 10 | | | | | 0 | | | 0 | | | 100 | | 1.70 +/− 0.77 |
| VEDRANTAIS | | | | | 0 | | | 0 | | | 100 | | 1.70 +/− 0.72 |
| VIRGOS | | | | | 96 | | 0.05 +/− 0.02 | 4 | | | 0 | | |
| FREE CUCUMBER | | | | | 100 | | 0.21 +/− 0.10 | 0 | | | 0 | | |

Legend:
X: type of cross; I: self-fertilization; BC: cross with the untransformed genotype TEZIER 10
GEN: generation; T0: primary transformant; T1: No.1 descendant; T2: No.2 descendant.
K: nptII gene; CP: capsid protein gene; RZ: polyribozyme 136; G: gus gene
+: presence; −: absence; QT: quantity
% G: percentage of plants expressing the gus gene
% R: percentage of resistant plants or plants without symptoms
% T: percentage of tolerant plants
% S: percentage of sensitive plants 1) Genetic Study of the Lines:

The level of expression of the gus gene enables the type of segregation and the state of homozygosity to be determined.

In the case of the two lines 88.105 and 153.8, the level of expression of the gus gene is 80% and 73%, respectively, in the T1 generation obtained by means of self-fertilization. This indicates a Mendelian type of segregation of a dominant gene (3:1) with the integration of the T-DNA at a single locus. Molecular analyses have shown the presence of a single copy of the T-DNA integrated into the plant genome.

Furthermore, the level of expression of the gus gene is 100% in the T2 generation for both lines, which confirms the state of homozygosity of the integrated gene.

In the case of line 146.42, the level of expression of the gus gene is 77% in the T1 generation obtained by self-fertilization, which shows a Mendelian type of segregation of a dominant gene with integration of the T-DNA at a single locus. Molecular analyses have shown the presence of several T-DNA and/or T-DNA fragments at a single locus of the plant genome.

Furthermore, the fact that the level of expression of the gus gene is 90% in the T2 generation emphasizes that the line tested is not homo-zygous for this integrated gene (Table 3). Homozygosity was obtained in T3 in the case of line 146.42. The level of expression of the gus gene for line 141.1 is 57% in the T1 generation obtained after crossing with the untransformed TEZIER 10.genotype. This also corresponds to a Mendelian type of segregation of a dominant gene (1:1) with integration of the T-DNA at a single locus. Molecular analyses have shown the presence of a single T-DNA integrated into the plant genome.

In the case of line 146.28, the level of expression of the gus gene is 73% in the T1 generation obtained after crossing with the untransformed TEZIER 10 genotype. This indicates a segregation of the dominant genes with integration of the T-DNA at several loci. Molecular analyses have shown the presence of several T-DNA or T-DNA fragments at two loci of the plant genome.

2) Behaviour vis-a-vis the Virus:

All of the resistant-type plants express the gus gene. Some of the sensitive plants express the gus gene (Table 3).

In the case of line 88.105, 25% of plants of the resistant type and 75% of sensitive plants were obtained in the T1 generation as a result of self-fertilization. This shows a Mendelian type of segregation of a recessive gene (1:3) for the resistance gene.

In the case of line 153.8, 55% of plants of the resistant type and 45% of sensitive plants were obtained in the T1 generation as a result of self-fertilization. It is difficult to come to a conclusion with regard to the resistance gene.

In the case of line 141.1, 40% of tolerant plants and 60% of sensitive plants were obtained in the T1 generation by crossing with the untransformed TEZIER 10 genotype. This indicates a Mendelian type of segregation of a dominant gene (1:1) for the resistance gene. The behaviour of the polyribozyme 136 is thus similar to that of the gus gene.

In the case of line 146.42, 79% of plants without symptoms and 21% of sensitive plants were obtained in the T1 generation as a result of self-fertilization. This implies a Mendelian type of segregation of a dominant gene (3:1) for the resistance gene. The behaviour of the ribozyme 136 is thus similar to that of the gus gene.

3) Estimation of the Quantities of Virus:

The quantities of virus detected by the ELISA assay are quite low in the plants without symptoms but nonetheless higher than those in the Free Cucumber resistant control (Table 10).

The tolerant plants contain appreciable quantities of virus.

The sensitive plants possess very high quantities of virus.

The plants expressing the polyribozymes (lines 146.42, T2 and T3) contain a smaller amount of virus than the plants of the resistant type expressing the capsid protein (line 153.8, T2).

It appears that there is a quite good correlation between the quantities of virus detected and the severity of the symptoms.

Figure 9:
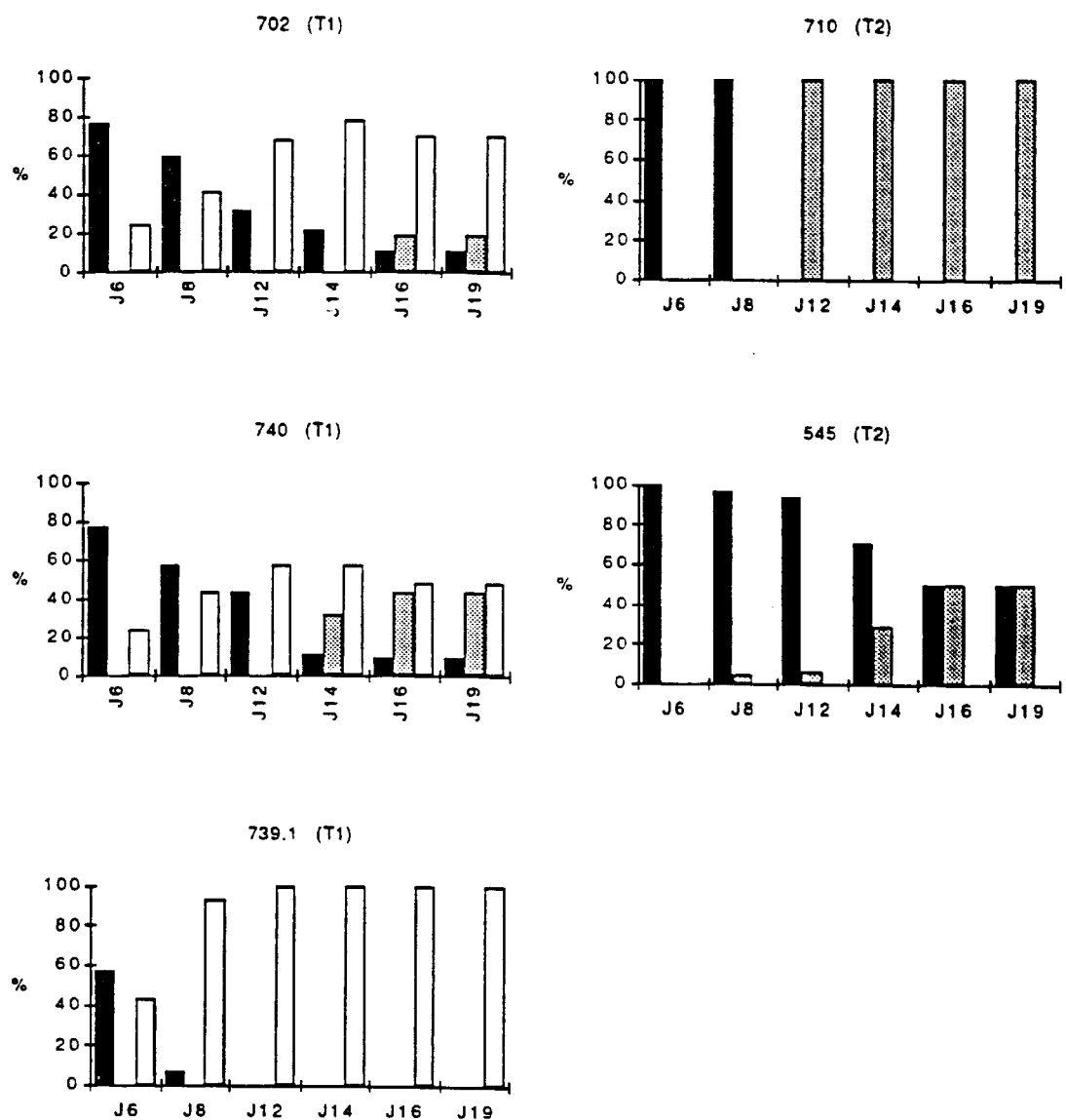

4) Development of the Symptoms of the CKV With Time:

T1 Plants of the lines mentioned in FIGS. 1 and 2 were infected with the CMV strain TL 28. The symptoms were recorded 6, 8, 12, 14, 16 and 19 days after inoculation. The results are presented in the histograms (FIGS. 9 and 10).

The values obtained after D16 show no further variation. In the case of the "capsid protein" lines, a more or less rapid diminution of the number of plants without symptoms is to be noted in favour of the appearance of plants with symptoms. In the case of the lines 88–105 and 153–8 in the T1 generation, on D16 and D14 respectively, tolerant plants develop characterized by the phenomenon of "recovery". Furthermore, in line 88–105 in the T2 generation, 100% of the plants without symptoms on D8 are converted into 100% of tolerant plants which subsist until D19 (FIG. 9).

This sudden change of the plants without symptoms into tolerant plants may be explained by a pronounced effect of the climatic conditions.

In line 153.8 in the T2 generation, a progressive appearance of tolerant plants is to be noted. From D16 onwards, 50% of the T2 plants are without symptoms and 50% are tolerant.

In the case of the "polyribozyme" lines, a diminution of the number of T1 plants without symptoms in favour of plants with symptoms is to be emphasized in lines 141.1 and 146.28 (FIG. 10).

Furthermore, in the case of line 141.1, 40% of tolerant T1 plants is to be noted from D16 onwards. In line 146.28, tolerant T2 plants develop from D14 to reach 26% on D16.

Moreover, in line 146.42, the T1 plants without symptoms represent 80% on D6 and remain almost stable with time (78% on D8, D12 and D14, 79% as of D16).

The T2 plants of line 146.42 exhibit a similar behaviour. This result shows the very high level of resistance of this line and stability of the resistance gene in the descendants.

In conclusion, two lines of the "resistant" type which express the gene for the capsid protein and one completely resistant line which expresses the polyribozyme 136 were obtained. In the case of the two lines expressing the gene for the capsid protein the resistance observed is more similar to tolerance than to complete resistance. In fact, some plants infected by the virus which exhibit severe symptoms are able to develop new healthy leaves under certain conditions.

No tolerance phenomenom is observed in the case of the completely resistant line which expresses the polyribozyme 136. In the case of the 2 lines which express the capsid protein, relatively high quantities of virus were observed in the resistant plants, whereas in the resistant plants which express the polyribozyme 136 the quantity of virus is almost the same as in the Free Cucumber resistant control.

Example 5

Resistance of Melon Lines in Generation T1, Which Express the Polyribozyme 165, to Infection by CMV Strain TL28:

The results obtained for 13 T1 lines expressing the polyribozyme 165, are presented in table 4 and show that:

after infection with TL28, 15 to 100% of the T1 individuals are without symptoms for 12 lines;

the phenomenom of "recovery" is only slightly present. Only 5 lines have between 6 and 60% T1 tolerants plants.

The majority of the lines expressing the polyribozyme 165 have been obtained by self-fertilisation. The expected theoretical frequency of polyribozyme 165 is 75% in T1 plants inoculated with CMV. The percentage of "resistant-type" plants varies between 15 and 100% according to the transgenic line.

In conclusion, as with the lines expressing the polyribozyme 136, a large number of lines expressing the polyribozyme 165 are without symptoms and have few tolerant plants. The polyribozyme 165 differs from the polyribozyme 136 by two additional functional ribozymes. The two constructions give similar results for resistance to infection by CMV.

TABLE 4

RESISTANCE OF T1 GENERATION MELON PLANTS EXPRESSING THE POLYRIBOZYME 165 TO INFECTION BY CMV STRAIN TL28

| LINES | CROSS | % R | % T | % S |
|---|---|---|---|---|
| 10.2 | I | 100 | 0 | 0 |
| 203.6 | BC | 0 | 0 | 100 |
| 205.1 | I | 50 | 45 | 5 |
| 205.3 | I | 66 | 0 | 34 |
| 206.1 | I | 94 | 6 | 0 |
| 207.3 | I | 61 | 0 | 39 |
| 207.5 | I | 80 | 0 | 20 |
| 207.7 | I | 64 | 0 | 36 |
| 207.8 | I | 69 | 9 | 22 |
| 207.9 | I | 100 | 0 | 0 |
| 211.1 | I | 15 | 0 | 85 |
| 212.1 | I | 87 | 13 | 0 |
| 215.1 | I | 20 | 60 | 20 |
| VEDRANTAIS | | 0 | 0 | 100 |
| VIRGOS | | 100 | 0 | 0 |
| FREE CUCUMBER | | 100 | 0 | 0 |

Legend:

I: self-fertilization

BC: cross with the untransformed genotype TELIZIER 10

% R: percentage of resistant plants or plants without symptoms

% T: percentage of tolerant plants

% S: percentage of sensitive plants

What is claimed is:

1. A polyribozyme having endoribonuclease activity and which inactivates the capsid protein gene of a plant virus, wherein the polyribozyme comprises a plurality of ribozymes, each of which cleaves the capsid protein gene or its corresponding transcript, or its corresponding replication intermediate, wherein each ribozyme comprises a catalytic portion and two hybridizing arms that are complementary to a portion of the capsid protein gene of the plant virus, wherein the plant virus is selected from the group consisting of: the Caulimoviruses, the Geminiviruses, the Reoviridae, the Rhabdoviridae, the Tobamoviruses, the Potexviruses, the Potyviruses, the Carlaviruses, the Closteroviruses, the Tobraviruses, the Hordeiviruses, the Tymoviruses, the Barley Yellow Dwarf Virus, the Tombusviruses, the Sobemoviruses, the Neopviruses, the Comoviruses, the Cucumoviruses, the Bromoviruses, and the Ilarviruses.

2. The polyribozyme according to claim 1 having the formula:

$$[(Y_1-Q-Y_2)-(S)_n]_p$$

wherein $Y_1$ and $Y_2$ are each a hybridizing arm having at least 4 bases and being complementary to a part of the capsid protein gene, a part of its corresponding transcript, or a part of its corresponding replication intermediate;

Q is the catalytic region of a ribozyme;

S is a nucleotide sequence which has between 2 and 500 bases and is not complementary to the capsid protein gene, its corresponding transcript or its corresponding replication Intermediate;

n=0 or 1; and p is an integer greater than 1.

3. The polyribozyme according to claim 1 wherein each ribozyme as selected from the group consisting of a hammerhead ribozyme and a hairpin ribozyme.

4. The polyribozyme according to claim 1 wherein each ribozyme targets an XUX site.

5. The polyribozyme according to claim 4 wherein the number of ribozymes is equal to or less than the total number of XUX sites present in the capsid protein gene, or in its corresponding transcript, or its corresponding replication intermediate.

6. The polyribozyme according to claim 5, wherein each ribozyme targets an XUX site which occurs in a zone of homology conserved between different strains of the same virus or between different viruses.

7. The polyribozyme according to claim 1, wherein the plant virus is selected from the group consisting of: Cauliflower Mosaic Virus (CaMV), Maize Streak Virus (MSV) Wound Tumor Virus (WTV), Potato Yellow Dwarf Virus (PYDV), Tomato Spotted Wilt Virus (TSWV), Tobacco Mosaic Virus (TMV), Potato Virus X (PXV), Potato Virus Y (PYV), Carnation Latent Virus (CLV), Beet Yellow Virus (BYV), Tobacco Rattle Virus (TRV), Barley Stripe Mosaic Virus (BSMV), Turnip Yellow Mosaic Virus (TYMV), Barley Yellow Dwarf Virus (BYDV), Tomato Bushy Stunt Virus (TBSV), Southern Bean Mosaic Virus (SBMV), Tobacco Necrosis Virus (TNV), Tobacco Ring Spot Virus (TRSV), Cow Pea Mosaic Virus (CPMV), Pea Enation Mosaic Virus (PEMV), Cucumber Mosaic Virus (CMV), Brome Mosaic Virus (BMV), and Tobacco Streak Virus (TSV).

8. The polyribozyme according to claim 7, wherein each hybridizing arm is complementary to the transcript of the capsid protein gene of the Cucumber Mosaic Virus.

9. The polyribozyme of claim 1 consisting of RNA.

10. A DNA molecule coding for a polyribozyme according to claim 1.

11. A process for rendering a slant resistant to a virus, which process comprises the introduction into the plant of the DNA of claim 10.

12. The process according to claim 11, wherein the introduction into the plant of he DNA is made by genetic transformation of a part of the plant by a DNA molecule coding for the polyribozyme, followed by regeneration of a transgenic plant.

13. The process according to claim 12, wherein the transformation is carried out by the intermediary of *Agrobacterium tumefaciens* or *Agrobacterium rhizogenes*.

14. A transgenic plant resistant to a virus, said plant containing in its genome a sequence which gives rise on transcription to the polyribozyme according to claim 1.

15. The transgenic plant according to claim 14, the plant being resistant to Cucumber Mosaic Virus.

16. The transgenic plant according to claim 15 which is a melon, a cucumber, a courgette, a tomato, a sweet pepper or a bean.

17. Transgenic fruit of the plant according to claim 14.

18. Transgenic fruit of the plant according to claim 15.

19. Transgenic seed of the plant according to claim 14.

20. Transgenic seed of the plant according to claim 15.

21. A plant cell transformed by the DNA according to claim 10.

* * * * *